United States Patent [19]

Lepone

[11] Patent Number: 4,528,024

[45] Date of Patent: Jul. 9, 1985

[54] HERBICIDAL ALKYL SULFONES

[75] Inventor: Gerald E. Lepone, Wilmington, Del.

[73] Assignee: E. I. Du Pont de Nemours and Company, Wilmington, Del.

[21] Appl. No.: 397,655

[22] Filed: Jul. 16, 1982

Related U.S. Application Data

[63] Continuation-in-part of Ser. No. 300,501, Sep. 9, 1981, abandoned.

[51] Int. Cl.³ .................... A01N 47/36; C07D 239/42
[52] U.S. Cl. ........................................ 71/92; 544/321; 544/323; 544/332
[58] Field of Search .................... 71/92; 544/321, 323, 544/332

[56] References Cited

U.S. PATENT DOCUMENTS

| 4,169,719 | 10/1979 | Levitt | 71/92 |
| 4,310,346 | 1/1982 | Levitt | 544/321 |
| 4,394,153 | 7/1983 | Reap | 71/92 |
| 4,394,506 | 7/1983 | Levitt | 71/92 |
| 4,419,121 | 12/1983 | Meyer et al. | 71/92 |
| 4,420,325 | 12/1983 | Sauers | 71/92 |
| 4,435,205 | 3/1984 | Reap | 71/92 |

FOREIGN PATENT DOCUMENTS

| 48143 | 3/1982 | European Pat. Off. | 544/321 |
| 57546 | 8/1982 | European Pat. Off. | 544/332 |

Primary Examiner—Robert Gerstl

[57] ABSTRACT

This invention relates to alkyl sulfones which have herbicidal activity and are also useful as plant-growth regulants.

14 Claims, No Drawings

HERBICIDAL ALKYL SULFONES

RELATED APPLICATION

This application is a continuation-in-part of my co-pending application U.S. Ser. No. 300,501, filed Sept. 9, 1981 now abandoned.

BACKGROUND OF THE INVENTION

This invention relates to alkyl sulfones which are useful as agricultural chemicals.

French Pat. No. 1,468,747 discloses the following para-substituted phenylsulfonamides, useful as antidiabetic agents:

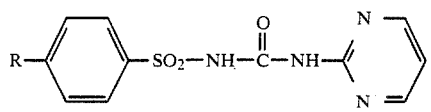

wherein $R=H$, halogen, $CF_3$ or alkyl.

Logemann et al., Chem. Ab., 53, 18052 g (1959), disclose a number of sulfonamides, including uracil derivatives and those having the formula:

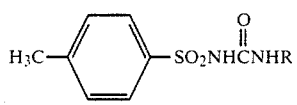

wherein
R is butyl, phenyl or

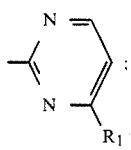

and
$R_1$ is hydrogen or methyl.

When tested for hypoglycemic effect in rats (oral doses of 25 mg/100 g), the compounds in which R is butyl and phenyl were most potent.

Wojciechowski, J. Acta, Polon. Pharm. 19, p. 121-5 (1962) [Chem. Ab., 59 1633 e] describes the synthesis of N-[(2,6-dimethoxypyrimidin-4-yl)aminocarbonyl]-4-methylbenzenesulfonamide:

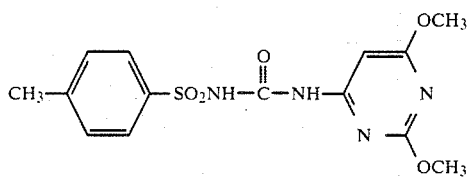

Based upon similarity to a known compound, the author predicted hypoglycemic activity for the foregoing compound.

Netherlands Pat. No. 121,788, published Sept. 15, 1966, teaches the preparation of compounds of Formula (i), and their use as general or selective herbicides,

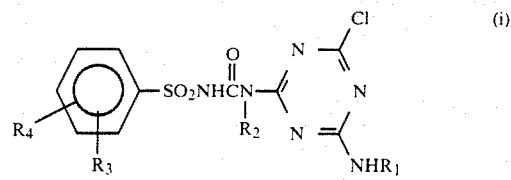

wherein
$R_1$ and $R_2$ may independently be alkyl of 1-4 carbon atoms; and
$R_3$ and $R_4$ may independently be hydrogen, chlorine or alkyl of 1-4 carbon atoms.

Compounds of Formula (ii), and their use as antidiabetic agents, are reported in *J. drug Res.* 6, 123 (1974),

wherein R is pyridyl.

In U.S. Ser. No. 029,821 now abandoned, herbicidal compounds such as N-heterocyclic-N'(arylsulfonyl)carbamimidothioates (or compounds wherein a thienyl radical is substituted for the aryl radical), such as methyl N'-(2-chlorophenyl)sulfonyl)-N-(4-methoxy-6-methylpyrimidin-2-yl)carbamimidothioate are taught.

U.S. Pat. No. 3,689,549 to R. P. Williams discloses "heterocyclic sulfonamides wherein the heteroatoms are inert can be used, e.g., compounds having the furan, thiophene or pyridine nucleus," in the production of sulfonyl isocyanates from sulfonamides in a sulfolane solvent.

B. G. Boggiano, V. Petrow, O. Stephenson and A. M. Wild, in *Journal of Pharmacy and Pharmacology* 13, 567-574 (1961) disclose the following compounds which were tested for hypoglycemic activity.

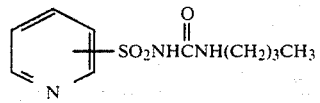

where

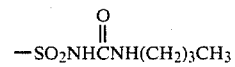

is in the 2 or 3 position.

J. Delarge in Acta Pol. Pharm. 34, 245-249 (1977) discloses N-alkylcarbamoylpyridinesulfonamides, as described in the structure below, as mild antiinflammatory agents and strong diuretics.

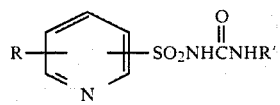

R=3-, 4-, 5-, 6-Me, 2-, 4-, 6-Cl, 3-Br, 4-$Et_2N$, 4-$Me_2CHNH$, 4-(3-$ClC_6H_4$)NH, 4-(3-$CF_3C_6H_4$)NH;
R'=Et, Pr, $Me_2CH$, Bu

in 2-, 3- and 4-position.

German Pat. No. 2,516,025 (Nov. 6, 1975) to J. E. Delarge, C. L. Lapiere and A. H. Georges discloses the following compounds as inflammation inhibitors and diuretics.

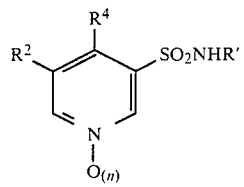

$R^4 = XR$ $R = C_6H_4R^3$ ($R^3 = $ Cl, $CF_3$, Me, MeO, H, Br, F, $NO_2$, Et, $NH_2$), Et, iso-Pr, 4-methylfuryl, $C_6H_3Cl_2-$, $C_6H_3(CF_3)Cl$;

$R' = $ alkylcarbamoyl, cyclohexylcarbamoyl, arylcarbamoyl, $CSNHCH_2CH=CH_2$, $CONHC_6H_4Cl$-p, alkylthiocarbamoyl, H, COEt;

$R^2 = $ H, Me;

X = NH, NMe, O, S, NEt; and n = 0, 1.

U.S. Pat. No. 3,346,590 (Oct. 10, 1967) (to K. Dickere and E. Kuhle) disclose the following pyridinesulfonyl isothiocyanates as novel compounds.

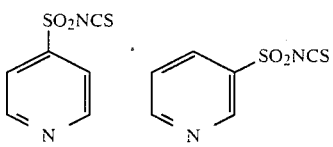

Chem. Abstr. 83 163951p (1975) reports preparation of several 3-substituted 2-alkylsulfonylpyridines:

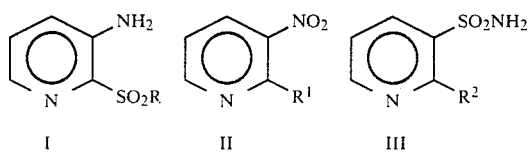

wherein $R = CH_3$ or $C_2H_5$;

$R^1 = $ SH, SR, $SO_2R$ or Cl; and $R^2 = $ Cl, SH or $SO_2C_2H_5$.

Compound II with $R^1 = SO_2C_2H_5$ is reported to give 96.9% inhibition of gluconeogenesis in rat renal cortex tissue.

U.S. Pat. No. 4,127,405 and U.S. Pat. No. 4,169,719 discloses herbicidal sulfonylureas of the general structure:

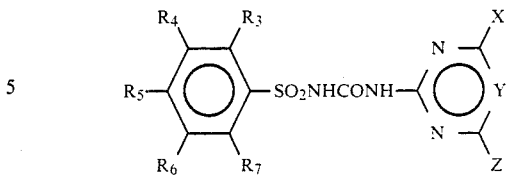

where, among others $R_3$ is $CH_3S(O)_n$ or $C_2H_5S(O)_n$, n being 0, 1 or 2.

U.S. Ser. No. 152,021 pending discloses herbicidal sulfonylureas of the general formula:

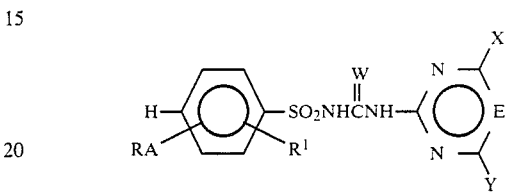

where

A is $S(O)_n$, n being 0, 1 or 2; and

R is $CHF_2$, $CF_3$, $CH_2CF_3$, $CF_2CHFG$, G being F, Cl, Br or $CF_3$.

U.S. Ser. No. 227,886 discloses herbicidal sulfonylureas of the general formula:

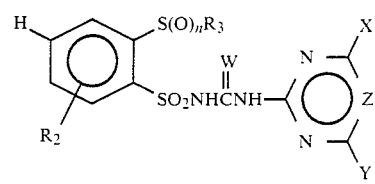

where $R_3$ is $C_3-C_4$ alkyl, $C_3-C_4$ alkenyl, cyclopropylmethyl or cyclopentyl; and n is 0, 1 or 2.

The presence of undesired vegetation causes substantial damage to useful crops, especially agricultural products that satisfy man's basic food needs, such as soybeans, barley, wheat, and the like. The current population explosion and concomitant world food shortage demand improvements in the efficiency of producing these crops. Prevention or minimizing the loss of a portion of valuable crops by killing, or inhibiting the growth of undesired vegetation is one way of improving this efficiency.

A wide variety of materials useful for killing, or inhibiting (controlling) the growth of undesired vegetation is available; such materials are commonly referred to as herbicides. The need exists, however, for still more effective herbicides that destroy or retard weeds without causing significant damage to useful crops.

SUMMARY OF THE INVENTION

This invention relates to novel compounds of Formula I and their agriculturally suitable salts, suitable agricultural compositions containing them, and their method of use as general and/or selective pre-emergence and/or post-emergence herbicides, and as plant-growth regulators.

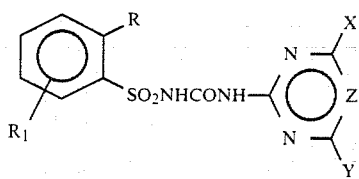  I wherein
R is S(O)$_n$CH(R$_2$)A;
A is OR$_3$, CH$_2$OR$_3$, OCH$_2$CH$_2$OCH$_3$, CH$_2$OCH$_2$-CH$_2$OCH$_3$, S(O)$_p$R$_3$, CH$_2$S(O)$_p$R$_3$, CO$_2$R$_3$, CH$_2$CO$_2$R$_3$, CN, CH$_2$CN,

CH$_2$OH, CH(OH)CH$_3$, CH$_2$CH$_2$OH, C(O)CH$_3$, CH$_2$C(O)CH$_3$, CHO, CH(OCH$_3$)$_2$ or

;

R$_1$ and R$_4$ are independently H, F, Cl, Br, CH$_3$, OCH$_3$, CF$_3$ or NO$_2$;
R$_2$ is H or CH$_3$;
R$_3$ is C$_1$-C$_2$ alkyl;
n is 0, 1 or 2;
p is 0, 1 or 2;
X is CH$_3$, OCH$_3$ or Cl;
Y is CH$_3$, C$_2$H$_5$, CH$_2$OCH$_3$, OCH$_3$, OC$_2$H$_5$, NH$_2$, NHCH$_3$ or N(CH$_3$)$_2$; and
Z is CH or N;
and their agriculturally suitable salts; provided that:
(1) when X is Cl then Z is CH;
(2) when X is Cl and Y is CH$_3$, C$_2$H$_5$, CH$_2$OCH$_3$, OCH$_3$ or OC$_2$H$_5$ then A is OCH$_2$CH$_2$OCH$_3$, CH$_2$OCH$_2$CH$_2$OCH$_3$, CO$_2$R$_3$, CH$_2$CO$_2$R$_3$, CN, CH$_2$CN,

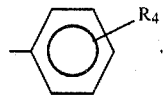

CH$_2$OH, CH(OH)CH$_3$, CH$_2$CH$_2$OH, C(O)CH$_3$, CH$_2$C(O)CH$_3$, CHO, CH(OCH$_3$)$_2$ or

;

(3) when X is Cl and A is OR$_3$, CH$_2$OR$_3$, S(O)$_p$R$_3$ or CH$_2$S(O)$_p$R$_3$, then Y is NH$_2$, NHCH$_3$ or N(CH$_3$)$_2$.

Preferred for reasons of their higher herbicidal activity or more favorable ease of synthesis are:
(1) Compounds of Formula I where A is OCH$_2$CH$_2$OCH$_3$, CH$_2$OCH$_2$CH$_2$OCH$_3$, CO$_2$R$_3$, CH$_2$CO$_2$R$_3$, CN, CH$_2$CH$_2$CN, CH(OH)CH$_3$,

CH$_2$OH, CH$_2$CH$_2$OH, C(O)CH$_3$, CH$_2$C(O)CH$_3$, CHO, CH(OCH$_3$)$_2$ or

(2) Compounds of Preferred 1 where A is CO$_2$R$_3$ or CN; R$_1$ is H; and X is not Cl.
(3) Compounds of Formula I where Y is NH$_2$, NHCH$_3$ or N(CH$_3$)$_2$.

Specifically preferred are:
N-[(4,6-dimethylpyrimidin-2-yl)aminocarbonyl]-2-(2-methoxyethylsulfonyl)benzenesulfonamide;
2-(2-methoxyethylsulfonyl)-N-[(4-methoxy-6-methylpyrimidin-2-yl)aminocarbonyl]benzenesulfonamide;
N-[(4,6-dimethoxypyrimidin-2-yl)aminocarbonyl]-2-(2-methoxyethylsulfonyl)benzenesulfonamide;
N-[(4,6-dimethyl-1,3,5-triazin-2-yl)aminocarbonyl]-2-(2-methoxyethylsulfonyl)benzenesulfonamide;
2-(2-methoxyethylsulfonyl)-N-[(4-methoxy-6-methyl-1,3,5-triazin-2-yl)aminocarbonyl]benzenesulfonamide;
N-[(4,6-dimethoxy-1,3,5-triazin-2-yl)aminocarbonyl]-2-(2-methoxyethylsulfonyl)benzenesulfonamide;
N-[(4,6-dimethylpyrimidin-2-yl)aminocarbonyl]-2-(cyanomethylthio)benzenesulfonamide;
N-[(4-methoxy-6-methylpyrimidin-2-yl)aminocarbonyl]-2-(cyanomethylthio)benzenesulfonamide;
N-[(4,6-dimethoxypyrimidin-2-yl)aminocarbonyl]-2-(cyanomethylthio)benzenesulfonamide;
N-[(4,6-dimethyl-1,3,5-triazin-2-yl)aminocarbonyl]-2-(cyanomethylthio)benzenesulfonamide;
N-[(4-methoxy-6-methyl-1,3,5-triazin-2-yl)aminocarbonyl]-2-(cyanomethylthio)benzenesulfonamide;
N-[(4,6-dimethoxy-1,3,5-triazin-2-yl)aminocarbonyl]-2-(cyanomethylthio)benzenesulfonamide;
N-[(4,6-dimethylpyrimidin-2-yl)aminocarbonyl]-2-(2-(methoxy-2-oxoethylsulfonyl)benzenesulfonamide;
N-[(4,6-dimethoxypyrimidin-2-yl)aminocarbonyl]-2-(2-methoxy-2-oxoethylsulfonyl)benzenesulfonamide; and
N-[(4-methoxy-6-methyl-1,3,5-triazin-2-yl)aminocarbonyl]-2-(2-methoxy-2-oxoethylsulfonyl)benzenesulfonamide.

SYNTHESIS

As shown in Equation 1, the compounds of Formula I, wherein R=SCH(R$_2$)A or R=SO$_2$CH(R$_2$)A, can be prepared by reacting an appropriately substituted sulfonyl isocyanate of Formula II with an appropriate 2-aminopyrimidine or 2-amino-1,3,5-triazine of Formula III, R, R$_1$, X, Y and Z being as defined above.

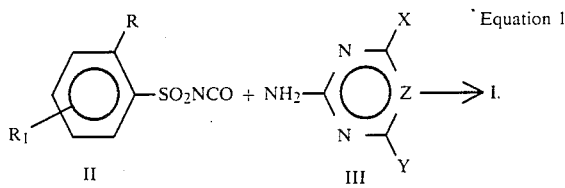

Equation 1

The reaction is best carried out in inert aprotic organic solvents such as methylene chloride, tetrahydrofuran or acetonitrile, at ambient pressure and temperature. The mode of addition is not critical; however, it is often convenient to add the sulfonyl isocyanate to a stirred suspension of amine III. Since such isocyanates are usually liquids, their addition can be easily controlled.

The reaction is generally exothermic. In some cases, the desired product is insoluble in the warm reaction medium and crystallizes from it in pure form. Products soluble in the reaction medium are isolated by evaporation of the solvent, trituration of the solid residue with solvents such as 1-chlorobutane or ethyl ether, and filtration.

The intermediate sulfonyl isocyanates of Formula II wherein n≠1 can be prepared as shown in Equation 2 by reacting the corresponding sulfonamides of Formula IV with phosgene in the presence of n-butyl isocyanate at reflux in a solvent such as xylene, according to the procedure of H. Ulrich and A. A. Y. Sayigh, *Newer Methods of Preparative Organic Chemistry*, Vol. VI, p. 223-241, Academic Press, New York and London, W. Foerst Ed. Alternatively, the reaction described in Equation 2 can be carried out in the presence of a catalytic amount of a tertiary organic amine, such as 1,4-diaza[2.2.2]bicyclooctane.

In cases where formation of the desired sulfonyl isocyanate is difficult by the above procedure, the sulfonylurea formed by the reaction of butyl isocyanate with the appropriate sulfonamide is treated with phosgene according to the above reference.

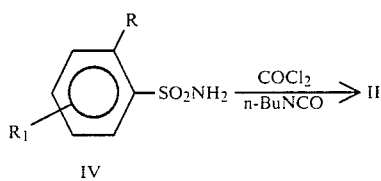

Equation 2

Compounds of Formula I may also be prepared from the sulfonamides of Formula IV and heterocyclic carbamates of Formula V as outlined in Equation 3. Treatment of IV with trimethylaluminum, followed by the addition of V will give compounds of Formula I after aqueous acidic workup. The carbamates of Formula V are readily prepared from the appropriate aminopyrimidine or aminotriazine by procedures well known in the art.

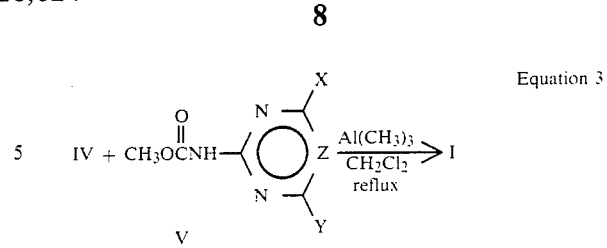

Equation 3

As shown in Equation 4, the compounds of Formula I can be prepared from the appropriate sulfonamides of Formula IV and heterocyclic amines of Formula III via the intermediate sulfonyl carbamates of Formula VI. Heating equimolar amounts of VI and III in a high boiling solvent, for example dioxane, will yield compounds of Formula I.

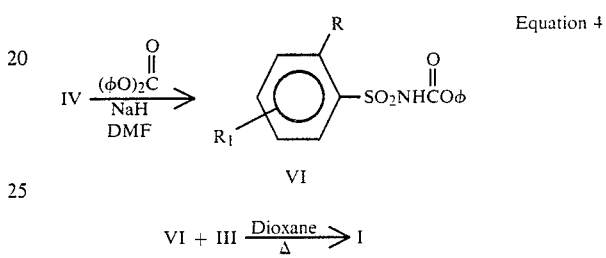

Equation 4

The sulfonamides of Formula IV can be prepared by a variety of procedures reported in the literature. As shown in Equation 5, the thioether of Formula VII may be prepared from the appropriate 2-aminothiophenol and an alkyl halide as described in the literature, e.g. R. N. Prasad, et al. *Can. J. Chem.* 44, 1247 (1966). The formation of the benzenesulfonyl chloride and the corresponding sulfonamide IVa has been previously described (co-pending application U.S. Ser. No. 192,034, filed Sept. 29, 1980). The oxidation of IVa to the corresponding 2-alkylsulfinyl or 2-alkylsulfonylbenzenesulfonamides of Formula IVb may be carried out utilizing a variety of standard literature procedures, including m-chloroperoxybenzoic acid (C. R. Johnson, et al., *Tetrahedron* 25, 5649 (1969)), or with aqueous hydrogen peroxide in acetic acid (F. G. Bordwell, et al., *J. Amer. Chem. Soc.* 77, 1141 (1955)).

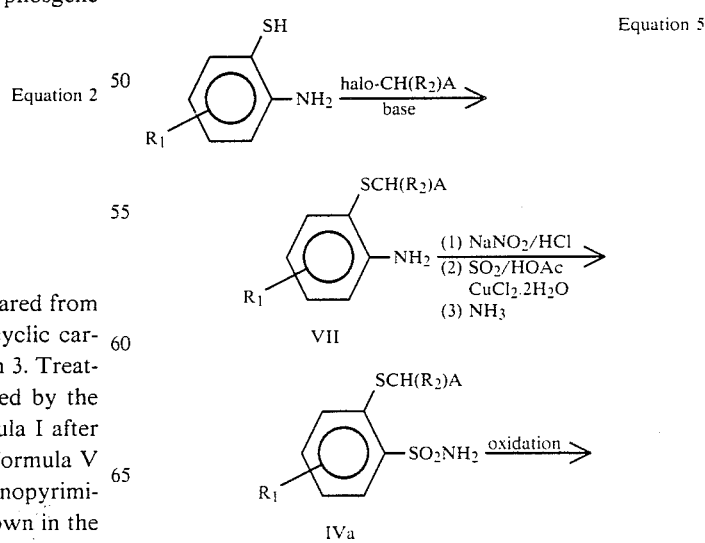

Equation 5

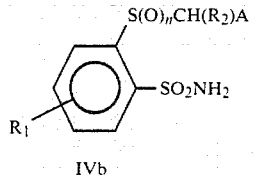

IVb n = 1,2

In some cases, diazotization of VII procedures more smoothly if oxidation is carried out first. As shown in Equation 6, protection of the amino group, for example as the acid amide, followed by oxidation, deprotection and then diazotization produces sulfonamide IVb.

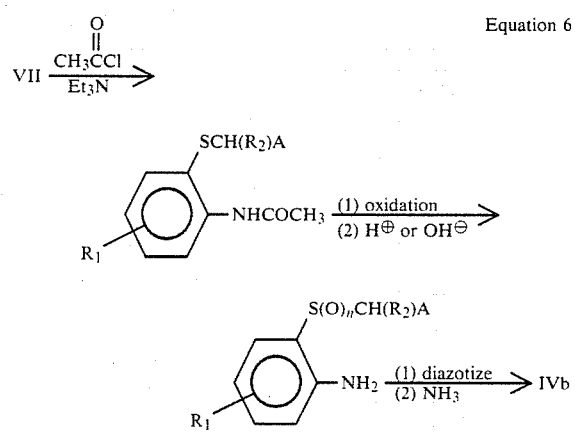

Equation 6 n = 1,2

Compounds of Formula IV wherein n≠1 may also be prepared from 2-halonitrobenzenes of Formula VIII as outlined in Equation 7. Halide displacement in VIII by thiols (n=0) or sulfinates (n=2) is widely reported in the literature (for general reviews see, "Organic Chemistry of Sulfur", S. Oae, ed., Plenum Press, New York, 1977, pp. 232-233; Reid, "Organic Chemistry of Bivalent Sulfur," Chemical Publishing Co., New York, Vol. 2, pp. 16-21, 24-29; Vol. 3, pp. 11-14; Peach, in Patai, "The Chemistry of the Thiol Group," pt. 2, pp. 735-744, John Wiley and Sons, Inc., New York, 1974).

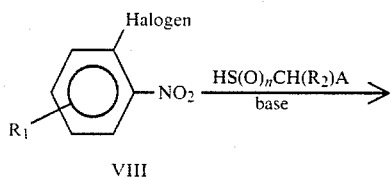

Equation 7

VIII

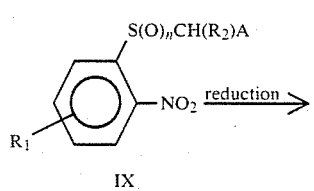

IX

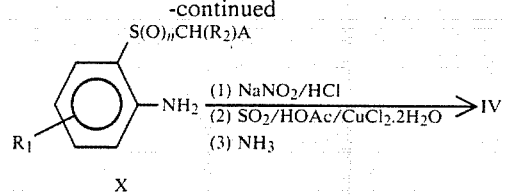

X

Compounds of Formula IX where n≠1 may also be prepared as shown in Equation 8 [in addition to references cited above, see, *Zh Obshch. Khim*, 35, (8) 1361 (1965) and *J. Chem. Soc.*, 763 (1946)]. Reduction of IX to the amine X can be carried out by a variety of standard literature procedures, including catalytic hydrogenation (Rylander, "Catalytic Hydrogenation over Platinum Metals," pp. 168-202, Academic Press, Inc., New York, 1967) and reduction with iron (D. Cowsley et al., *Synthesis* 118 (1977)) or stannous chloride (*Org. Synth., Coll. Vol.* 2, 130 (1943); ibid, 3, 240, 453 (1955)) in acidic medium. Compounds of Formula IX wherein n=0 may also be oxidized to the corresponding sulfones prior to reduction.

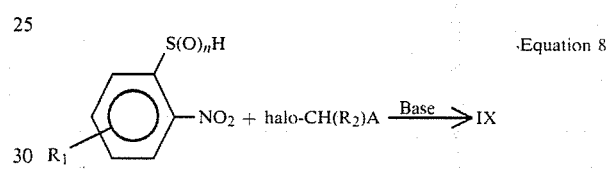

Equation 8

Ortho-lithiation of appropriately substituted benzene derivatives also provides a route to sulfonamides of Formula IV. As shown in Equation 9, the N-t-butylbenzenesulfonamides of Formula XI may be ortholithiated [for general review, see H. W. Gschwend et al., *Organic Reactions*, 26, 1 (1979)] and then trapped with sulfur, followed by alkyl halide, or disulfide to give sulfonamides of Formula IVa [S. Gronowitz et al., *Acta, Chem. Scand.* 21, 812 (1967) and *Chem. Ber.*, 99, 3215 (1966)]. Treatment of XII with sulfur dioxide, followed by alkyl halide will give sulfonamides of Formula IVb [*JACS*, 74, 5177 (1952)].

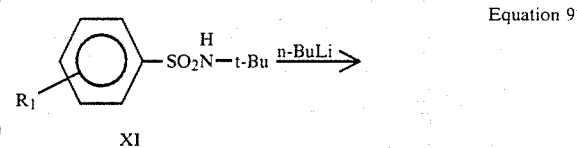

Equation 9

XI

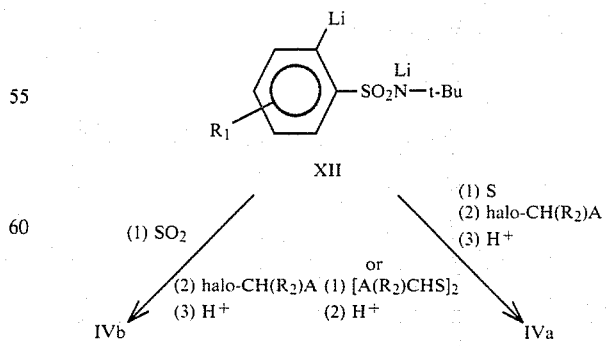

The lithium sulfonates of Formula XIII can also be ortholithiated to give compounds of Formula XIV as shown in Equation 10. Treatment of XIV with sulfur electrophiles as in Equation 9 will give the sulfonates of Formula XV [for example, see J. C. Martin et al., *JOC*, 45, 3728 (1980)]. Conversion of XV to the sulfonamides of Formula IV can be accomplished using thionyl chloride and a catalytic amount of dimethylformamide and then treating the sulfonyl chloride with ammonia.

Equation 10

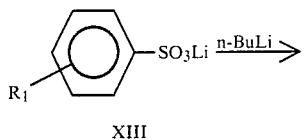

XIII

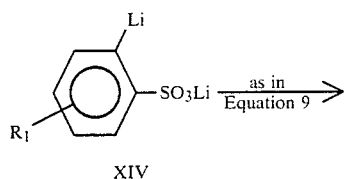

XIV

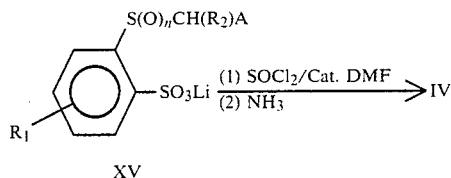

XV

Sulfonamides of Formula IV may also be prepared from chlorosulfonamides of Formula XVI (see U.S. Pat. No. 4,127,405 and U.S. Pat. No. 4,169,719 for preparation of XVI) and the appropriate mercaptan of Formula XVII as shown in Equation 11. Heating XVI and XVII in a high boiling solvent, for example dimethylformamide, in the presence of two equivalents of base will give IVa after acidic workup. Oxidation of IVa will yield sulfonamides of Formula IVb.

Equation 11

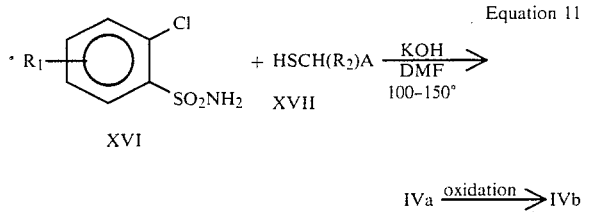

XVI

IVa $\xrightarrow{\text{oxidation}}$ IVb

Compounds of Formula I may also be prepared by the reaction of the substituted sulfonamides of Formula IV with an appropriate heterocyclic isocyanate as previously described (co-pending applications U.S. Ser. No. 098,725 and U.S. Ser. No. 098,722, filed Nov. 30, 1979).

Compounds of Formula Ib, where $R = SOCH(R_2)A$ can be prepared from the appropriate compounds of Formula Ia wherein $R = SCH(R_2)A$ by oxidation with m-chloroperoxybenzoic acid as shown in Equation 12. The reaction can be carried out by stirring equivalent amounts of Ia with m-chloroperoxybenzoic acid (MCPBA) in an inert solvent such as chloroform at 0° to reflux for 12-24 hours. The insoluble m-chlorobenzoic acid produced is removed by filtration and the chloroform solution is concentrated to yield the crude product. Purification by standard techniques will give the desired product. Oxidation of Ia with one equivalent of hydrogen peroxide in acetic acid at room temperature will also give the sulfoxides Ib.

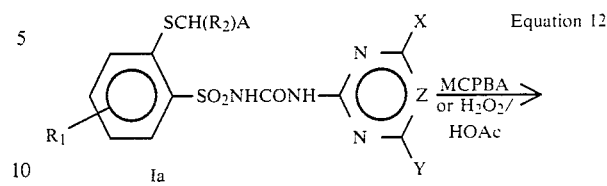

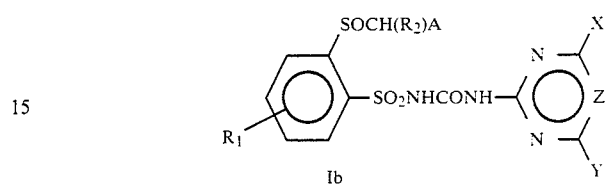

Compounds of Formula I wherein A represents a hydroxyalkyl group are most readily prepared from the corresponding protected alcohols. For example, treatment of Ic with dilute acid will yield the hydroxyethyl compounds of Formula Id as shown in Equation 13. The choice of alcohol protecting group need not be limited to the tetrahydropyranyl group, as would be readily apparent to one skilled in the art. The compounds of Formula Ic may be prepared by methods taught in Equations 1-12.

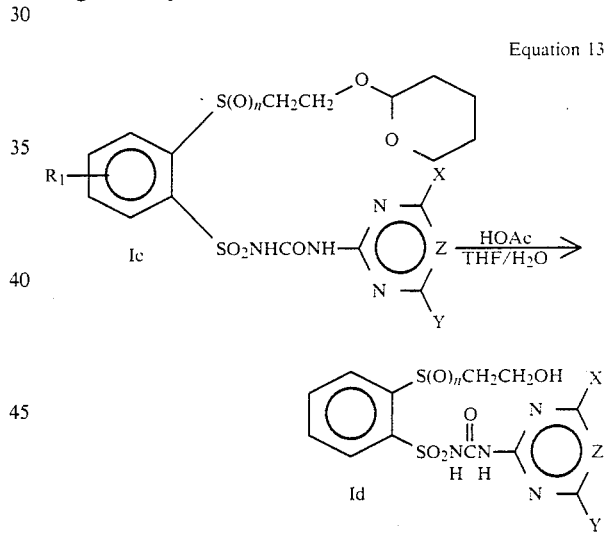

The synthesis of heterocyclic amine derivatives has been reviewed in "The Chemistry of Heterocyclic Compounds," a series published by Interscience Publ., New York and London. 2-Aminopyrimidines are described by D. J. Brown in "The Pyrimidines", Vol. XVI of the above series. 2-Amino-1,3,5-triazines can be synthesized according to the methods described by E. M. Smolin and L. Rapaport in "s-Triazines and Derivatives," Vol. XIII of the same series.

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide, carbonate or hydroxide). Quaternary amine salts can be made by similar techniques.

Salts of compounds of Formula I can also be prepared by exchange of one cation for another. Cationic exchange can be effected by direct contact of an aqueous solution of a salt of a compound of Formula I (e.g., alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a compound of Formula I (e.g., an alkali metal or quaternary amine salt) through a column packed with a cation exchange resin containing the cation to be exchanged for that of the original salt and the desired product is eluted from the column. This method is particularly useful when the desired salt is water-soluble.

Acid addition salts, useful in this invention, can be obtained by reacting a compound of Formula I with a suitable acid, e.g., p-toluenesulfonic acid, trichloroacetic acid or the like.

The compounds of this invention and their preparation are further illustrated by the following examples wherein temperatures are given in degrees centigrade and parts are by weight unless otherwise designated.

EXAMPLE 1

2-(2-Methoxyethylthio)benzenamine

To a solution of 2-aminothiophenol (93%, 123 g, 0.910 mol) and sodium hydroxide (40.2 g, 1.00 mol) in 90% aqueous ethanol (637 ml) was added dropwise 2-bromoethylmethylether (127 g, 0.910 mol) at room temperature. When the addition was complete, the reaction mixture was refluxed for 2 hours, cooled to room temperature, and then concentrated in vacuo. The resulting residue was diluted with water (1400 ml) and extracted with methylene chloride ($3 \times 500$ ml). The extracts were washed with water ($2 \times 500$ ml) and brine (500 ml), dried with ($MgSO_4$), filtered and concentrated to give a dark oil. Distillation of the crude product gave 2-(2-methoxyethylthio)benzenamine (148 g, 89%) as a light yellow oil; bp 90°–103° (0.1 mm).

NMR ($CDCl_3$)δ: 2.85 (t, $SCH_2$), 3.1–3.6 (m, $CH_2OCH_3$); 4.4 (broad s, $NH_2$); 6.0–7.5 (m, Ar-H).

IR (neat): 3400 (NH), 3300 (NH), 2900, 1600, 1470, 1440, 1300, 1110 and 750 cm$^{-1}$.

EXAMPLE 2

2-(2-Methoxyethylthio)benzenesulfonamide

To a suspension of 2-(2-methoxyethylthio)benzenamine (91.5 g, 0.500 mol) in a mixture of concentrated hydrochloric acid (175 ml) and glacial acetic acid (80 ml) was added a solution of sodium nitrite (39.3 g, 0.550 mol) in water (75 ml) at −5° to 0°. The solution was stirred at 0° for ½ hour and then poured, in several portions, into a mixture of cupric chloride dihydrate (10.0 g, 0.059 mol) and liquid sulfur dioxide (77.5 ml, 1.76 mol), in glacial acetic acid (500 ml) at 0°. The resulting solution was stirred at 0° for one hour and then allowed to warm to room temperature. After four hours, ice-water (2000 ml) was added and the resulting oil was extracted into 1-chlorobutane ($4 \times 500$ ml). The organic extracts were washed with water ($5 \times 500$ ml) and saturated sodium bicarbonate (until neutral), dried ($MgSO_4$), filtered and reduced in volume to 1000 ml. The sulfonyl chloride solution was cooled to 0° under nitrogen and treated with liquid anhydrous ammonia (50 ml, 2.0 mol). After 1 hour at 0°, the mixture was allowed to warm to room temperature and stirred for 2½ hours. The reaction mixture was filtered and the resulting solid washed with 1-chlorobutane and water. 2-(2-methoxyethylthio)benzenesulfonamide (84 g, 68%) was obtained as a light-orange solid: m.p. 127°–130°.

NMR ($CDCl_3$/DMSO)δ: 3.1–3.9 (m, with s at 3.4, 7H, $SCH_2CH_2OCH_3$); 6.2–6.9 (broad, 1.9H, $NH_2$); 7.2–8.2 (m, 4.6H, Ar—H);

IR (KBr): 3250 ($NH_2$), 3050, 1550, 1420, 1320 ($SO_2$), 1160 ($SO_2$), 1100, 1050 and 755 cm$^{-1}$.

EXAMPLE 3

2-[(2-Methoxyethyl)sulfonyl]benzenesulfonamide

To a solution of 2-[(2-methoxyethyl)thio]benzenesulfonamide (10.0 g, 40.5 mol) in chloroform (200 ml), previously cooled to 0° to 5° under nitrogen, was added with stirring, m-chloroperoxybenzoic acid (85%, 19.7 g, 0.0970 mol) in chloroform (200 ml), added dropwise over 45 minutes. After 1 hour at 0°, the mixture was allowed to warm to room temperature and stirred for 72 hours. The reaction mixture was filtered, washed with 10% sodium sulfite (until it tested negative for peroxides), 5% aqueous sodium bicarbonate; it was then dried ($Na_2SO_4$), filtered and concentrated in vacuo. 2-[(2-Methoxyethyl)sulfonyl]benzenesulfonamide (10.0 g, 88%) was obtained as a white powder, m.p. 120°–123°.

NMR ($CDCl_3$/DMSO)δ: 3.2 (s, 3H, $OCH_3$); 3.6–4.1 (m, 4.2H, $SO_2CH_2CH_2$); 6.9 (broad s, 1.7H, $NH_2$); 7.6–8.4 (m, 4.3H, Ar—H)

IR (KBr) 3300–3200 (d, $NH_2$), 1540, 1340 ($SO_2$), 1300 ($SO_2$), 1160 ($SO_2$), 1110 ($SO_2$), 1040, 780, 750, 730 and 700 cm$^{-1}$.

EXAMPLE 4

2-[(2-Methoxyethyl)sulfonyl]benzenesulfonyl isocyanate

A mixture of 2-[(2-methoxyethyl)sulfonyl]benzenesulfonamide (9.5 g, 0.034 mol), n-butylisocyanate (4.7 ml, 0.041 mol) and 1,4-diaza[2.2.2]bicyclooctane (0.1 g) in mixed xylenes (58 ml) was heated to 140° with stirring under nitrogen. Liquid phosgene (2.7 ml, 0.039 mol) was added at a rate to maintain an internal temperature between 125°–135°. When the addition was complete, the solution was refluxed for 2 hours, cooled to room temperature under nitrogen purge and then filtered under a nitrogen atmosphere. Removal of solvent in vacuo gave 2-[(2-methoxyethyl)sulfonyl]benzenesulfonyl isocyanate, which was used immediately in Example 5 below, without further purification.

IR (neat): 2250 cm$^{-1}$ (N=C=O).

EXAMPLE 5

N-[(4,6-Dimethoxypyrimidin-2-yl)aminocarbonyl]-2-[(2-methoxyethyl)sulfonyl]benzenesulfonamide A solution of 2-[(2-methoxyethyl)sulfonyl]benzenesulfonyl isocyanate (1.7 g, 0.0057 mol) in dichloromethane (10 ml) was added to 2-amino-4,6-dimethoxypyrimidine (0.70 g, 0.0045 mol) and DABCO (catalytic amount); the mixture was stirred at room temperature under nitrogen overnight. Filtration gave N-[(4,6-dimethoxypyrimidin-2-yl)aminocarbonyl]-2-[(2-methoxyethyl)sulfonyl]benzenesulfonamide (1.43 g) as a white powder, m.p. 187°–192°.

NMR (DMSO/$CDCl_3$)δ: 3.1 (s, $OCH_3$); 3.4–4.4 (m with s at 3.9, $SO_2CH_2CH_2$, het—$OCH_3$); 5.9 (s, het—H); 7.8–8.6 (m, Ar—H);

IR (KBr) 1720 (c=o), 1600, 1580, 1440, 1350 (SO$_2$), 1320 (SO$_2$), 1220, 1170 (SO$_2$) and 1150 (SO$_2$) cm$^{-1}$.

EXAMPLE 6

N-[(4,6-Dimethoxypyrimidin-2-yl)aminocarbonyl]-2-(2-methoxy-2-oxoethylsulfonyl)benzenesulfonamide

A solution of 2-(2-methoxy-2-oxoethylsulfonyl)benzenesulfonyl isocyanate (2.6 mmol) in dichloromethane (5 ml) was added to 2-amino-4,6-dimethoxypyrimidine (0.31 g, 2.0 mmol) and DABCO (catalytic amount). After stirring at room temperature under nitrogen overnight, the reaction mixture was filtered giving 0.4 g of a white powder, m.p. 175°–179°.

NMR (DMSO/CDCl$_3$)δ: 3.6 (s, CO$_2$CH$_3$); 3.95 (s, het—OCH$_3$); 4.8 (s, SO$_2$CH$_2$); 5.9 (s, het—H); 7.8–8.6 (m, Ar—H); 10.5 (broad s, NH);

IR (KBr) 1700 (c=o), 1600, 1430, 1350 (SO$_2$), 1310 (SO$_2$), and 1160 (SO$_2$) cm$^{-1}$.

Using procedures similar to those described in Examples 1–6 and Equations 1–13, the following compounds in Tables I–II may be prepared by one skilled in the art.

TABLE I

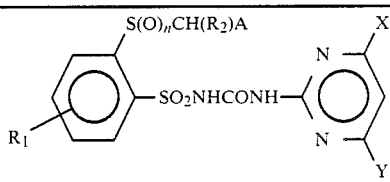

| A | R$_1$ | R$_2$ | n | X | Y | m.p. (°C.) |
|---|---|---|---|---|---|---|
| OCH$_3$ | H | H | 0 | CH$_3$ | CH$_3$ | |
| OCH$_3$ | H | H | 0 | CH$_3$ | OCH$_3$ | |
| OCH$_3$ | H | H | 0 | OCH$_3$ | OCH$_3$ | |
| OCH$_3$ | H | H | 1 | CH$_3$ | CH$_3$ | |
| OCH$_3$ | H | H | 1 | CH$_3$ | OCH$_3$ | |
| OCH$_3$ | H | H | 1 | OCH$_3$ | OCH$_3$ | |
| OCH$_3$ | H | H | 2 | CH$_3$ | CH$_3$ | |
| OCH$_3$ | H | H | 2 | CH$_3$ | OCH$_3$ | |
| OCH$_3$ | H | H | 2 | OCH$_3$ | OCH$_3$ | 140–141° (D) |
| OC$_2$H$_5$ | H | H | 0 | CH$_3$ | CH$_3$ | |
| OC$_2$H$_5$ | H | H | 0 | CH$_3$ | OCH$_3$ | |
| OC$_2$H$_5$ | H | H | 0 | OCH$_3$ | OCH$_3$ | |
| OC$_2$H$_5$ | H | H | 1 | CH$_3$ | CH$_3$ | |
| OC$_2$H$_5$ | H | H | 1 | CH$_3$ | OCH$_3$ | |
| OC$_2$H$_5$ | H | H | 1 | OCH$_3$ | OCH$_3$ | |
| OC$_2$H$_5$ | H | H | 2 | CH$_3$ | CH$_3$ | |
| OC$_2$H$_5$ | H | H | 2 | CH$_3$ | OCH$_3$ | |
| OC$_2$H$_5$ | H | H | 2 | OCH$_3$ | OCH$_3$ | |
| CH$_2$OCH$_3$ | H | H | 0 | CH$_3$ | CH$_3$ | 189–192° |
| CH$_2$OCH$_3$ | H | H | 0 | CH$_3$ | OCH$_3$ | 130–134° |
| CH$_2$OCH$_3$ | H | H | 0 | OCH$_3$ | OCH$_3$ | 182–185° |
| CH$_2$OCH$_3$ | H | H | 1 | CH$_3$ | CH$_3$ | |
| CH$_2$OCH$_3$ | H | H | 1 | CH$_3$ | OCH$_3$ | |
| CH$_2$OCH$_3$ | H | H | 1 | OCH$_3$ | OCH$_3$ | |
| CH$_2$OCH$_3$ | H | H | 2 | CH$_3$ | CH$_3$ | 188–189.5° (D) |
| CH$_2$OCH$_3$ | H | H | 2 | CH$_3$ | OCH$_3$ | 178–181° |
| CH$_2$OCH$_3$ | H | H | 2 | OCH$_3$ | OCH$_3$ | 187–192° |
| CH$_2$OC$_2$H$_5$ | H | H | 0 | CH$_3$ | CH$_3$ | |
| CH$_2$OC$_2$H$_5$ | H | H | 0 | CH$_3$ | OCH$_3$ | |
| CH$_2$OC$_2$H$_5$ | H | H | 0 | OCH$_3$ | OCH$_3$ | |
| CH$_2$OC$_2$H$_5$ | H | H | 1 | CH$_3$ | CH$_3$ | |
| CH$_2$OC$_2$H$_5$ | H | H | 1 | CH$_3$ | OCH$_3$ | |
| CH$_2$OC$_2$H$_5$ | H | H | 1 | OCH$_3$ | OCH$_3$ | |
| CH$_2$OC$_2$H$_5$ | H | H | 2 | CH$_3$ | CH$_3$ | |
| CH$_2$OC$_2$H$_5$ | H | H | 2 | CH$_3$ | OCH$_3$ | |
| CH$_2$OC$_2$H$_5$ | H | H | 2 | OCH$_3$ | OCH$_3$ | |
| OCH$_2$CH$_2$OCH$_3$ | H | H | 0 | CH$_3$ | CH$_3$ | |
| OCH$_2$CH$_2$OCH$_3$ | H | H | 0 | CH$_3$ | OCH$_3$ | |
| OCH$_2$CH$_2$OCH$_3$ | H | H | 0 | OCH$_3$ | OCH$_3$ | |
| OCH$_2$CH$_2$OCH$_3$ | H | H | 1 | CH$_3$ | CH$_3$ | |
| OCH$_2$CH$_2$OCH$_3$ | H | H | 1 | CH$_3$ | OCH$_3$ | |
| OCH$_2$CH$_2$OCH$_3$ | H | H | 1 | OCH$_3$ | OCH$_3$ | |
| OCH$_2$CH$_2$OCH$_3$ | H | H | 2 | CH$_3$ | CH$_3$ | |
| OCH$_2$CH$_2$OCH$_3$ | H | H | 2 | CH$_3$ | OCH$_3$ | |
| OCH$_2$CH$_2$OCH$_3$ | H | H | 2 | OCH$_3$ | OCH$_3$ | |
| CH$_2$OCH$_2$CH$_2$OCH$_3$ | H | H | 0 | CH$_3$ | CH$_3$ | |
| CH$_2$OCH$_2$CH$_2$OCH$_3$ | H | H | 0 | CH$_3$ | OCH$_3$ | |
| CH$_2$OCH$_2$CH$_2$OCH$_3$ | H | H | 0 | OCH$_3$ | OCH$_3$ | |
| CH$_2$OCH$_2$CH$_2$OCH$_3$ | H | H | 1 | CH$_3$ | CH$_3$ | |
| CH$_2$OCH$_2$CH$_2$OCH$_3$ | H | H | 1 | CH$_3$ | OCH$_3$ | |
| CH$_2$OCH$_2$CH$_2$OCH$_3$ | H | H | 1 | OCH$_3$ | OCH$_3$ | |
| CH$_2$OCH$_2$CH$_2$OCH$_3$ | H | H | 2 | CH$_3$ | CH$_3$ | |
| CH$_2$OCH$_2$CH$_2$OCH$_3$ | H | H | 2 | CH$_3$ | OCH$_3$ | |
| CH$_2$OCH$_2$CH$_2$OCH$_3$ | H | H | 2 | OCH$_3$ | OCH$_3$ | |
| SCH$_3$ | H | H | 0 | CH$_3$ | CH$_3$ | |
| SCH$_3$ | H | H | 0 | CH$_3$ | OCH$_3$ | |
| SCH$_3$ | H | H | 0 | OCH$_3$ | OCH$_3$ | |
| SOCH$_3$ | H | H | 1 | CH$_3$ | CH$_3$ | |

TABLE I-continued

[Structure: benzene ring with S(O)$_n$CH(R$_2$)A substituent, R$_1$ substituent, and SO$_2$NHCONH- linked to a pyrimidine with X and Y substituents]

| A | R$_1$ | R$_2$ | n | X | Y | m.p. (°C.) |
|---|---|---|---|---|---|---|
| SOCH$_3$ | H | H | 1 | CH$_3$ | OCH$_3$ | |
| SOCH$_3$ | H | H | 1 | OCH$_3$ | OCH$_3$ | |
| SO$_2$CH$_3$ | H | H | 2 | CH$_3$ | CH$_3$ | 121–140° |
| SO$_2$CH$_3$ | H | H | 2 | CH$_3$ | OCH$_3$ | |
| SO$_2$CH$_3$ | H | H | 2 | OCH$_3$ | OCH$_3$ | |
| SC$_2$H$_5$ | H | H | 0 | CH$_3$ | CH$_3$ | |
| SC$_2$H$_5$ | H | H | 0 | CH$_3$ | OCH$_3$ | |
| SC$_2$H$_5$ | H | H | 0 | OCH$_3$ | OCH$_3$ | |
| SOC$_2$H$_5$ | H | H | 1 | CH$_3$ | CH$_3$ | |
| SOC$_2$H$_5$ | H | H | 1 | CH$_3$ | OCH$_3$ | |
| SOC$_2$H$_5$ | H | H | 1 | OCH$_3$ | OCH$_3$ | |
| SO$_2$C$_2$H$_5$ | H | H | 2 | CH$_3$ | CH$_3$ | |
| SO$_2$C$_2$H$_5$ | H | H | 2 | CH$_3$ | OCH$_3$ | |
| SO$_2$C$_2$H$_5$ | H | H | 2 | OCH$_3$ | OCH$_3$ | |
| SCH$_3$ | H | H | 2 | CH$_3$ | CH$_3$ | |
| SCH$_3$ | H | H | 2 | CH$_3$ | OCH$_3$ | |
| SCH$_3$ | H | H | 2 | OCH$_3$ | OCH$_3$ | |
| SOCH$_3$ | H | H | 2 | CH$_3$ | CH$_3$ | |
| SOCH$_3$ | H | H | 2 | CH$_3$ | OCH$_3$ | |
| SOCH$_3$ | H | H | 2 | OCH$_3$ | OCH$_3$ | |
| CH$_2$SCH$_3$ | H | H | 0 | CH$_3$ | CH$_3$ | |
| CH$_2$SCH$_3$ | H | H | 0 | CH$_3$ | OCH$_3$ | |
| CH$_2$SCH$_3$ | H | H | 0 | OCH$_3$ | OCH$_3$ | |
| CH$_2$SOCH$_3$ | H | H | 1 | CH$_3$ | CH$_3$ | |
| CH$_2$SOCH$_3$ | H | H | 1 | CH$_3$ | OCH$_3$ | |
| CH$_2$SOCH$_3$ | H | H | 1 | OCH$_3$ | OCH$_3$ | |
| CH$_2$SO$_2$CH$_3$ | H | H | 2 | CH$_3$ | CH$_3$ | |
| CH$_2$SO$_2$CH$_3$ | H | H | 2 | CH$_3$ | OCH$_3$ | |
| CH$_2$SO$_2$CH$_3$ | H | H | 2 | OCH$_3$ | OCH$_3$ | |
| CH$_2$SC$_2$H$_5$ | H | H | 0 | CH$_3$ | CH$_3$ | |
| CH$_2$SC$_2$H$_5$ | H | H | 0 | CH$_3$ | OCH$_3$ | |
| CH$_2$SC$_2$H$_5$ | H | H | 0 | OCH$_3$ | OCH$_3$ | |
| CH$_2$SOC$_2$H$_5$ | H | H | 1 | CH$_3$ | CH$_3$ | |
| CH$_2$SOC$_2$H$_5$ | H | H | 1 | CH$_3$ | OCH$_3$ | |
| CH$_2$SOC$_2$H$_5$ | H | H | 1 | OCH$_3$ | OCH$_3$ | |
| CH$_2$SO$_2$C$_2$H$_5$ | H | H | 2 | CH$_3$ | CH$_3$ | |
| CH$_2$SO$_2$C$_2$H$_5$ | H | H | 2 | CH$_3$ | OCH$_3$ | |
| CH$_2$SO$_2$C$_2$H$_5$ | H | H | 2 | OCH$_3$ | OCH$_3$ | |
| CO$_2$CH$_3$ | H | H | 0 | CH$_3$ | CH$_3$ | 179–181° (D) |
| CO$_2$CH$_3$ | H | H | 0 | CH$_3$ | OCH$_3$ | |
| CO$_2$CH$_3$ | H | H | 0 | OCH$_3$ | OCH$_3$ | 182–185° |
| CO$_2$CH$_3$ | H | H | 1 | CH$_3$ | CH$_3$ | |
| CO$_2$CH$_3$ | H | H | 1 | CH$_3$ | OCH$_3$ | |
| CO$_2$CH$_3$ | H | H | 1 | OCH$_3$ | OCH$_3$ | |
| CO$_2$CH$_3$ | H | H | 2 | CH$_3$ | CH$_3$ | oil (IR 1730 & 1700 cm$^{-1}$) |
| CO$_2$CH$_3$ | H | H | 2 | CH$_3$ | OCH$_3$ | |
| CO$_2$CH$_3$ | H | H | 2 | OCH$_3$ | OCH$_3$ | 175–179° |
| CO$_2$C$_2$H$_5$ | H | H | 0 | CH$_3$ | CH$_3$ | |
| CO$_2$C$_2$H$_5$ | H | H | 0 | CH$_3$ | OCH$_3$ | |
| CO$_2$C$_2$H$_5$ | H | H | 0 | OCH$_3$ | OCH$_3$ | |
| CO$_2$C$_2$H$_5$ | H | H | 1 | CH$_3$ | CH$_3$ | |
| CO$_2$C$_2$H$_5$ | H | H | 1 | CH$_3$ | OCH$_3$ | |
| CO$_2$C$_2$H$_5$ | H | H | 1 | OCH$_3$ | OCH$_3$ | |
| CO$_2$C$_2$H$_5$ | H | H | 2 | CH$_3$ | CH$_3$ | |
| CO$_2$C$_2$H$_5$ | H | H | 2 | CH$_3$ | OCH$_3$ | |
| CO$_2$C$_2$H$_5$ | H | H | 2 | OCH$_3$ | OCH$_3$ | |
| CH$_2$CO$_2$CH$_3$ | H | H | 0 | CH$_3$ | CH$_3$ | |
| CH$_2$CO$_2$CH$_3$ | H | H | 0 | CH$_3$ | OCH$_3$ | |
| CH$_2$CO$_2$CH$_3$ | H | H | 0 | OCH$_3$ | OCH$_3$ | |
| CH$_2$CO$_2$CH$_3$ | H | H | 1 | CH$_3$ | CH$_3$ | |
| CH$_2$CO$_2$CH$_3$ | H | H | 1 | CH$_3$ | OCH$_3$ | |
| CH$_2$CO$_2$CH$_3$ | H | H | 1 | OCH$_3$ | OCH$_3$ | |
| CH$_2$CO$_2$CH$_3$ | H | H | 2 | CH$_3$ | CH$_3$ | |
| CH$_2$CO$_2$CH$_3$ | H | H | 2 | CH$_3$ | OCH$_3$ | |
| CH$_2$CO$_2$CH$_3$ | H | H | 2 | OCH$_3$ | OCH$_3$ | |
| CH$_2$CO$_2$C$_2$H$_5$ | H | H | 0 | CH$_3$ | CH$_3$ | |
| CH$_2$CO$_2$C$_2$H$_5$ | H | H | 0 | CH$_3$ | OCH$_3$ | |
| CH$_2$CO$_2$C$_2$H$_5$ | H | H | 0 | OCH$_3$ | OCH$_3$ | |
| CH$_2$CO$_2$C$_2$H$_5$ | H | H | 1 | CH$_3$ | CH$_3$ | |
| CH$_2$CO$_2$C$_2$H$_5$ | H | H | 1 | CH$_3$ | OCH$_3$ | |
| CH$_2$CO$_2$C$_2$H$_5$ | H | H | 1 | OCH$_3$ | OCH$_3$ | |

TABLE I-continued structure: benzene ring with S(O)ₙCH(R₂)A at ortho, SO₂NHCONH- linking to pyrimidine with X and Y at 4,6 positions; R₁ on benzene

| A | R₁ | R₂ | n | X | Y | m.p. (°C.) |
|---|----|----|---|---|---|------------|
| CH₂CO₂C₂H₅ | H | H | 2 | CH₃ | CH₃ | |
| CH₂CO₂C₂H₅ | H | H | 2 | CH₃ | OCH₃ | |
| CH₂CO₂C₂H₅ | H | H | 2 | OCH₃ | OCH₃ | |
| CN | H | H | 0 | CH₃ | CH₃ | 184–186° (D) |
| CN | H | H | 0 | CH₃ | OCH₃ | 194–195° |
| CN | H | H | 0 | OCH₃ | OCH₃ | 172–173° |
| CN | H | H | 1 | CH₃ | CH₃ | 180–183° (D) |
| CN | H | H | 1 | CH₃ | OCH₃ | 169–173° (D) |
| CN | H | H | 1 | OCH₃ | CH₃ | 204–207° (D) |
| CN | H | H | 2 | CH₃ | CH₃ | 205–207° (D) |
| CN | H | H | 2 | CH₃ | OCH₃ | 190–193° |
| CN | H | H | 2 | OCH₃ | OCH₃ | 220–221° |
| CH₂CN | H | H | 0 | CH₃ | CH₃ | |
| CH₂CN | H | H | 0 | CH₃ | OCH₃ | |
| CH₂CN | H | H | 0 | OCH₃ | OCH₃ | |
| CH₂CN | H | H | 1 | CH₃ | CH₃ | |
| CH₂CN | H | H | 1 | CH₃ | OCH₃ | |
| CH₂CN | H | H | 1 | OCH₃ | OCH₃ | |
| CH₂CN | H | H | 2 | CH₃ | CH₃ | |
| CH₂CN | H | H | 2 | CH₃ | OCH₃ | |
| CH₂CN | H | H | 2 | OCH₃ | OCH₃ | |
| —C₆H₅ | H | H | 0 | CH₃ | CH₃ | |
| —C₆H₅ | H | H | 0 | CH₃ | OCH₃ | |
| —C₆H₅ | H | H | 0 | OCH₃ | OCH₃ | |
| —C₆H₅ | H | H | 1 | CH₃ | CH₃ | |
| —C₆H₅ | H | H | 1 | CH₃ | OCH₃ | |
| —C₆H₅ | H | H | 1 | OCH₃ | OCH₃ | |
| —C₆H₅ | H | H | 2 | CH₃ | CH₃ | 166–172° |
| —C₆H₅ | H | H | 2 | CH₃ | OCH₃ | 163–168° |
| —C₆H₅ | H | H | 2 | OCH₃ | OCH₃ | 168–175° |
| —C₆H₄—OCH₃ | H | H | 0 | CH₃ | CH₃ | |
| —C₆H₄—OCH₃ | H | H | 0 | CH₃ | OCH₃ | |
| —C₆H₄—OCH₃ | H | H | 0 | OCH₃ | OCH₃ | |

TABLE I-continued $$\underset{R_1}{\underset{\diagdown}{\text{Ph}}}\overset{S(O)_n CH(R_2)A}{\underset{SO_2NHCONH-\overset{N}{\underset{N}{\diagdown}}}{\diagup}}\overset{X}{\underset{Y}{\diagdown}}$$

| A | R₁ | R₂ | n | X | Y | m.p. (°C.) |
|---|---|---|---|---|---|---|
| —C₆H₄—OCH₃ (p) | H | H | 1 | CH₃ | CH₃ | |
| —C₆H₄—OCH₃ (p) | H | H | 1 | CH₃ | OCH₃ | |
| —C₆H₄—OCH₃ (p) | H | H | 1 | OCH₃ | OCH₃ | |
| —C₆H₄—OCH₃ (p) | H | H | 2 | CH₃ | CH₃ | 172–177 (D) |
| —C₆H₄—OCH₃ (p) | H | H | 2 | CH₃ | OCH₃ | 174–177° |
| —C₆H₄—OCH₃ (p) | H | H | 2 | OCH₃ | OCH₃ | 171–175° |
| —C₆H₄—Cl (o) | H | H | 0 | CH₃ | CH₃ | |
| —C₆H₄—Cl (o) | H | H | 0 | CH₃ | OCH₃ | |
| —C₆H₄—Cl (o) | H | H | 0 | OCH₃ | OCH₃ | |
| —C₆H₄—Cl (o) | H | H | 2 | CH₃ | CH₃ | |
| —C₆H₄—Cl (o) | H | H | 2 | CH₃ | OCH₃ | |
| —C₆H₄—Cl (o) | H | H | 2 | OCH₃ | OCH₃ | |
| —C₆H₄—CH₃ (p) | H | H | 2 | CH₃ | CH₃ | |
| —C₆H₄—CH₃ (p) | H | H | 2 | CH₃ | OCH₃ | |
| —C₆H₄—CH₃ (p) | H | H | 2 | OCH₃ | OCH₃ | |

TABLE I-continued

![Structure: benzene ring with S(O)ₙCH(R₂)A at top, SO₂NHCONH-pyrimidine (X, Y substituents) at right, R₁ on ring]

| A | R₁ | R₂ | n | X | Y | m.p. (°C.) |
|---|---|---|---|---|---|---|
| 2-NO₂-phenyl | H | H | 2 | CH₃ | CH₃ | |
| 2-NO₂-phenyl | H | H | 2 | CH₃ | OCH₃ | |
| 2-NO₂-phenyl | H | H | 2 | OCH₃ | CH₃ | |
| 4-CF₃-phenyl | H | H | 2 | CH₃ | CH₃ | |
| 4-CF₃-phenyl | H | H | 2 | CH₃ | OCH₃ | |
| 4-CF₃-phenyl | H | H | 2 | OCH₃ | OCH₃ | |
| 2-F-phenyl | H | H | 2 | CH₃ | CH₃ | |
| 2-F-phenyl | H | H | 2 | CH₃ | OCH₃ | |
| 2-F-phenyl | H | H | 2 | OCH₃ | OCH₃ | |
| 4-Br-phenyl | H | H | 2 | CH₃ | CH₃ | |
| 4-Br-phenyl | H | H | 2 | CH₃ | OCH₃ | |
| 4-Br-phenyl | H | H | 2 | OCH₃ | OCH₃ | |
| 3-NO₂-phenyl | H | H | 0 | CH₃ | CH₃ | |
| 3-NO₂-phenyl | H | H | 0 | CH₃ | OCH₃ | |

TABLE I-continued $$\underset{R_1}{\text{Ar}}\text{-}SO_2NHCONH\text{-}\underset{Y}{\overset{X}{\text{Pyr}}}$$

with $S(O)_n CH(R_2)A$ ortho substituent

| A | R₁ | R₂ | n | X | Y | m.p. (°C.) |
|---|---|---|---|---|---|---|
| 2-NO₂-C₆H₄- | H | H | 0 | OCH₃ | OCH₃ | |
| 2-NO₂-C₆H₄- | H | H | 2 | CH₃ | CH₃ | |
| 2-NO₂-C₆H₄- | H | H | 2 | CH₃ | OCH₃ | |
| 2-NO₂-C₆H₄- | H | H | 2 | OCH₃ | OCH₃ | |
| 2-OCH₃-C₆H₄- | H | H | 2 | CH₃ | CH₃ | |
| 2-OCH₃-C₆H₄- | H | H | 2 | CH₃ | OCH₃ | |
| 2-OCH₃-C₆H₄- | H | H | 2 | OCH₃ | OCH₃ | |
| 2-CH₃-C₆H₄- | 5-F | CH₃ | 2 | CH₃ | CH₃ | |
| 2-CH₃-C₆H₄- | 5-Cl | CH₃ | 2 | CH₃ | OCH₃ | |
| 2-CH₃-C₆H₄- | 5-Br | CH₃ | 2 | OCH₃ | OCH₃ | |
| CH₂OCH₃ | 5-CH₃ | CH₃ | 2 | CH₃ | C₂H₅ | |
| CH₂OCH₃ | 5-OCH₃ | CH₃ | 2 | CH₃ | CH₂OCH₃ | |
| CH₂OCH₃ | 5-CF₃ | CH₃ | 2 | CH₃ | OC₂H₅ | |
| CH₂OCH₃ | 5-NO₂ | CH₃ | 2 | OCH₃ | CH₃ | |
| CH₂OCH₃ | 4-CH₃ | CH₃ | 2 | CH₃ | CH₃ | |
| CH₂OCH₃ | 4-OCH₃ | CH₃ | 2 | OCH₃ | OC₂H₅ | |
| OCH₃ | 6-Cl | CH₃ | 0 | OCH₃ | CH₂OCH₃ | |
| OCH₃ | 6-CH₃ | CH₃ | 1 | OCH₃ | OCH₃ | |
| CO₂CH₃ | 3-Br | CH₃ | 2 | OCH₃ | CH₃ | |
| CH₂CO₂C₂H₅ | 5-CH₃ | CH₃ | 2 | CH₃ | CH₂OCH₃ | |
| SO₂CH₃ | 5-CF₃ | CH₃ | 2 | CH₃ | OC₂H₅ | |
| CH₂SO₂CH₃ | 5-Cl | CH₃ | 2 | OCH₃ | OCH₃ | |
| CN | 5-CF₃ | CH₃ | 2 | OCH₃ | OCH₃ | |
| CH₂CN | 5-NO₂ | CH₃ | 2 | CH₃ | CH₃ | |

TABLE I-continued $$\underset{R_1}{\text{[benzene ring]}}\text{-}S(O)_n CH(R_2)A, SO_2NHCONH\text{-}\underset{Y}{\overset{X}{\text{[pyrimidine]}}}$$

| A | R₁ | R₂ | n | X | Y | m.p. (°C.) |
|---|---|---|---|---|---|---|
| 4-NO₂-C₆H₄- | H | H | 2 | CH₃ | CH₃ | |
| 4-NO₂-C₆H₄- | H | H | 2 | CH₃ | OCH₃ | |
| 4-NO₂-C₆H₄- | H | H | 2 | OCH₃ | OCH₃ | |
| 2-OCH₃-C₆H₄- | H | H | 2 | CH₃ | CH₃ | |
| 2-OCH₃-C₆H₄- | H | H | 2 | CH₃ | OCH₃ | |
| 2-OCH₃-C₆H₄- | H | H | 2 | OCH₃ | OCH₃ | |
| 2-CH₃-C₆H₄- | H | H | 2 | CH₃ | CH₃ | |
| 2-CH₃-C₆H₄- | H | H | 2 | CH₃ | OCH₃ | |
| 2-CH₃-C₆H₄- | H | H | 2 | OCH₃ | OCH₃ | |
| 2-Cl-C₆H₄- | H | H | 2 | CH₃ | CH₃ | |
| 2-Cl-C₆H₄- | H | H | 2 | CH₃ | OCH₃ | |
| 2-Cl-C₆H₄- | H | H | 2 | OCH₃ | OCH₃ | |
| CH₂OH | H | H | 0 | CH₃ | CH₃ | |
| CH₂OH | H | H | 0 | CH₃ | OCH₃ | |
| CH₂OH | H | H | 0 | OCH₃ | OCH₃ | |
| CH₂OH | H | H | 1 | CH₃ | CH₃ | |
| CH₂OH | H | H | 1 | CH₃ | OCH₃ | |
| CH₂OH | H | H | 1 | OCH₃ | OCH₃ | |
| CH₂OH | H | H | 2 | CH₃ | CH₃ | |
| CH₂OH | H | H | 2 | CH₃ | OCH₃ | |
| CH₂OH | H | H | 2 | OCH₃ | OCH₃ | |
| CH(OH)CH₃ | H | H | 0 | CH₃ | CH₃ | |
| CH(OH)CH₃ | H | H | 0 | CH₃ | OCH₃ | |
| CH(OH)CH₃ | H | H | 0 | OCH₃ | OCH₃ | |
| CH(OH)CH₃ | H | H | 1 | CH₃ | CH₃ | |
| CH(OH)CH₃ | H | H | 1 | CH₃ | OCH₃ | |

TABLE I-continued $$\underset{R_1}{\text{[phenyl ring with }S(O)_n CH(R_2)A\text{ substituent]}} - SO_2NHCONH - \underset{Y}{\overset{X}{\text{[pyrimidine ring]}}}$$

| A | $R_1$ | $R_2$ | n | X | Y | m.p. (°C.) |
|---|---|---|---|---|---|---|
| CH(OH)CH$_3$ | H | H | 1 | OCH$_3$ | OCH$_3$ | |
| CH(OH)CH$_3$ | H | H | 2 | CH$_3$ | CH$_3$ | |
| CH(OH)CH$_3$ | H | H | 2 | CH$_3$ | OCH$_3$ | |
| CH(OH)CH$_3$ | H | H | 2 | OCH$_3$ | OCH$_3$ | |
| CH$_2$CH$_2$OH | H | H | 0 | CH$_3$ | CH$_3$ | |
| CH$_2$CH$_2$OH | H | H | 0 | CH$_3$ | OCH$_3$ | |
| CH$_2$CH$_2$OH | H | H | 0 | OCH$_3$ | OCH$_3$ | |
| CH$_2$CH$_2$OH | H | H | 1 | CH$_3$ | CH$_3$ | |
| CH$_2$CH$_2$OH | H | H | 1 | CH$_3$ | OCH$_3$ | |
| CH$_2$CH$_2$OH | H | H | 1 | OCH$_3$ | OCH$_3$ | |
| CH$_2$CH$_2$OH | H | H | 2 | CH$_3$ | CH$_3$ | |
| CH$_2$CH$_2$OH | H | H | 2 | CH$_3$ | OCH$_3$ | |
| CH$_2$CH$_2$OH | H | H | 2 | OCH$_3$ | OCH$_3$ | |
| C(O)CH$_3$ | H | H | 0 | CH$_3$ | CH$_3$ | |
| C(O)CH$_3$ | H | H | 0 | CH$_3$ | OCH$_3$ | |
| C(O)CH$_3$ | H | H | 0 | OCH$_3$ | OCH$_3$ | |
| C(O)CH$_3$ | H | H | 1 | CH$_3$ | CH$_3$ | |
| C(O)CH$_3$ | H | H | 1 | CH$_3$ | OCH$_3$ | |
| C(O)CH$_3$ | H | H | 1 | OCH$_3$ | OCH$_3$ | |
| C(O)CH$_3$ | H | H | 2 | CH$_3$ | CH$_3$ | |
| C(O)CH$_3$ | H | H | 2 | CH$_3$ | OCH$_3$ | |
| C(O)CH$_3$ | H | H | 2 | OCH$_3$ | OCH$_3$ | |
| CH$_2$C(O)CH$_3$ | H | H | 0 | CH$_3$ | CH$_3$ | |
| CH$_2$C(O)CH$_3$ | H | H | 0 | CH$_3$ | OCH$_3$ | |
| CH$_2$C(O)CH$_3$ | H | H | 0 | OCH$_3$ | OCH$_3$ | |
| CH$_2$C(O)CH$_3$ | H | H | 1 | CH$_3$ | CH$_3$ | |
| CH$_2$C(O)CH$_3$ | H | H | 1 | CH$_3$ | OCH$_3$ | |
| CH$_2$C(O)CH$_3$ | H | H | 1 | OCH$_3$ | OCH$_3$ | |
| CH$_2$C(O)CH$_3$ | H | H | 2 | CH$_3$ | CH$_3$ | |
| CH$_2$C(O)CH$_3$ | H | H | 2 | CH$_3$ | OCH$_3$ | |
| CH$_2$C(O)CH$_3$ | H | H | 2 | OCH$_3$ | OCH$_3$ | |
| CHO | H | H | 0 | CH$_3$ | CH$_3$ | |
| CHO | H | H | 0 | CH$_3$ | OCH$_3$ | |
| CHO | H | H | 0 | OCH$_3$ | OCH$_3$ | |
| CHO | H | H | 1 | CH$_3$ | CH$_3$ | |
| CHO | H | H | 1 | CH$_3$ | OCH$_3$ | |
| CHO | H | H | 1 | OCH$_3$ | OCH$_3$ | |
| CHO | H | H | 2 | CH$_3$ | CH$_3$ | |
| CHO | H | H | 2 | CH$_3$ | OCH$_3$ | |
| CHO | H | H | 2 | OCH$_3$ | OCH$_3$ | |
| CH(OCH$_3$)$_2$ | H | H | 0 | CH$_3$ | CH$_3$ | |
| CH(OCH$_3$)$_2$ | H | H | 0 | CH$_3$ | OCH$_3$ | |
| CH(OCH$_3$)$_2$ | H | H | 0 | OCH$_3$ | OCH$_3$ | |
| CH(OCH$_3$)$_2$ | H | H | 1 | CH$_3$ | CH$_3$ | |
| CH(OCH$_3$)$_2$ | H | H | 1 | CH$_3$ | OCH$_3$ | |
| CH(OCH$_3$)$_2$ | H | H | 1 | OCH$_3$ | OCH$_3$ | |
| CH(OCH$_3$)$_2$ | H | H | 2 | CH$_3$ | CH$_3$ | |
| CH(OCH$_3$)$_2$ | H | H | 2 | CH$_3$ | OCH$_3$ | |
| CH(OCH$_3$)$_2$ | H | H | 2 | OCH$_3$ | OCH$_3$ | |
| CH(O—CH$_2$—CH$_2$—O) (1,3-dioxolane) | H | H | 0 | CH$_3$ | CH$_3$ | |
| CH(O—CH$_2$—CH$_2$—O) (1,3-dioxolane) | H | H | 0 | CH$_3$ | OCH$_3$ | |
| CH(O—CH$_2$—CH$_2$—O) (1,3-dioxolane) | H | H | 0 | OCH$_3$ | OCH$_3$ | |

TABLE I-continued

Structure: benzene ring with S(O)$_n$CH(R$_2$)A substituent, SO$_2$NHCONH- linked to pyrimidine with X and Y substituents, and R$_1$ on benzene.

| A | R$_1$ | R$_2$ | n | X | Y | m.p. (°C.) |
|---|---|---|---|---|---|---|
| CH(OCH$_2$CH$_2$O) (1,3-dioxolan-2-yl) | H | H | 1 | CH$_3$ | CH$_3$ | |
| CH(OCH$_2$CH$_2$O) | H | H | 1 | CH$_3$ | OCH$_3$ | |
| CH(OCH$_2$CH$_2$O) | H | H | 1 | OCH$_3$ | OCH$_3$ | |
| CH(OCH$_2$CH$_2$O) | H | H | 2 | CH$_3$ | CH$_3$ | |
| CH(OCH$_2$CH$_2$O) | H | H | 2 | CH$_3$ | OCH$_3$ | |
| CH(OCH$_2$CH$_2$O) | H | H | 2 | OCH$_3$ | OCH$_3$ | |
| OCH$_3$ | H | H | 2 | CH$_3$ | NH$_2$ | |
| CH$_2$OCH$_3$ | H | H | 2 | OCH$_3$ | NH$_2$ | |
| OCH$_2$CH$_2$OCH$_3$ | H | H | 2 | CH$_3$ | NH$_2$ | |
| CH$_2$OCH$_2$CH$_2$OCH$_3$ | H | H | 2 | OCH$_3$ | NH$_2$ | |
| SO$_2$CH$_3$ | H | H | 2 | CH$_3$ | NH$_2$ | |
| CH$_2$SO$_2$CH$_3$ | H | H | 2 | OCH$_3$ | NH$_2$ | |
| CO$_2$CH$_3$ | H | H | 2 | CH$_3$ | NH$_2$ | |
| CH$_2$CO$_2$CH$_3$ | H | H | 2 | OCH$_3$ | NH$_2$ | |
| CN | H | H | 2 | CH$_3$ | NH$_2$ | |
| CH$_2$CN | H | H | 2 | OCH$_3$ | NH$_2$ | |
| CH$_2$OH | H | H | 2 | CH$_3$ | NH$_2$ | |
| CH(OH)CH$_3$ | H | H | 2 | OCH$_3$ | NH$_2$ | |
| CH$_2$CH$_2$OH | H | H | 2 | CH$_3$ | NH$_2$ | |
| C(O)CH$_3$ | H | H | 2 | OCH$_3$ | NH$_2$ | |
| CH$_2$C(O)CH$_3$ | H | H | 2 | CH$_3$ | NH$_2$ | |
| CHO | H | H | 2 | OCH$_3$ | NH$_2$ | |
| CH(OCH$_3$)$_2$ | H | H | 2 | CH$_3$ | NH$_2$ | |
| OCH$_3$ | H | H | 2 | CH$_3$ | NHCH$_3$ | |
| CH$_2$OCH$_3$ | H | H | 2 | OCH$_3$ | NHCH$_3$ | |
| OCH$_2$CH$_2$OCH$_3$ | H | H | 2 | CH$_3$ | NHCH$_3$ | |
| CH$_2$OCH$_2$CH$_2$OCH$_3$ | H | H | 2 | OCH$_3$ | NHCH$_3$ | |
| SO$_2$CH$_3$ | H | H | 2 | CH$_3$ | NHCH$_3$ | |
| CH$_2$SO$_2$CH$_3$ | H | H | 2 | OCH$_3$ | NHCH$_3$ | |
| CO$_2$CH$_3$ | H | H | 2 | CH$_3$ | NHCH$_3$ | |
| CH$_2$CO$_2$CH$_3$ | H | H | 2 | OCH$_3$ | NHCH$_3$ | |
| CN | H | H | 2 | CH$_3$ | NHCH$_3$ | |
| CH$_2$CN | H | H | 2 | OCH$_3$ | NHCH$_3$ | |
| CH$_2$OH | H | H | 2 | CH$_3$ | NHCH$_3$ | |
| CH(OH)CH$_3$ | H | H | 2 | OCH$_3$ | NHCH$_3$ | |
| CH$_2$CH$_2$OH | H | H | 2 | CH$_3$ | NHCH$_3$ | |
| C(O)CH$_3$ | H | H | 2 | OCH$_3$ | NHCH$_3$ | |
| CH$_2$C(O)CH$_3$ | H | H | 2 | CH$_3$ | NHCH$_3$ | |
| CHO | H | H | 2 | OCH$_3$ | NHCH$_3$ | |

TABLE I-continued $$\underset{R_1}{\underset{|}{\text{benzene}}}\overset{S(O)_n CH(R_2)A}{\underset{SO_2NHCONH-}{}}\text{-pyrimidine}\overset{X}{\underset{Y}{}}$$

| A | $R_1$ | $R_2$ | n | X | Y | m.p. (°C.) |
|---|---|---|---|---|---|---|
| $CH(OCH_3)_2$ | H | H | 2 | $CH_3$ | $NHCH_3$ | |
| $\begin{array}{c}O\\ /\\ CH\\ \backslash\\ O\end{array}$ (dioxolane) | H | H | 2 | $OCH_3$ | $NHCH_3$ | |
| $OCH_3$ | H | H | 2 | $CH_3$ | $N(CH_3)_2$ | |
| $CH_2OCH_3$ | H | H | 2 | $OCH_3$ | $N(CH_3)_2$ | |
| $OCH_2CH_2OCH_3$ | H | H | 2 | $CH_3$ | $N(CH_3)_2$ | |
| $CH_2OCH_2CH_2OCH_3$ | H | H | 2 | $OCH_3$ | $N(CH_3)_2$ | |
| $SO_2CH_3$ | H | H | 2 | $CH_3$ | $N(CH_3)_2$ | |
| $CH_2SO_2CH_3$ | H | H | 2 | $OCH_3$ | $N(CH_3)_2$ | |
| $CO_2CH_3$ | H | H | 2 | $CH_3$ | $N(CH_3)_2$ | |
| $CH_2CO_2CH_3$ | H | H | 2 | $OCH_3$ | $N(CH_3)_2$ | |
| $CN$ | H | H | 2 | $CH_3$ | $N(CH_3)_2$ | |
| $CH_2CN$ | H | H | 2 | $OCH_3$ | $N(CH_3)_2$ | |
| $CH_2OH$ | H | H | 2 | $CH_3$ | $N(CH_3)_2$ | |
| $CH(OH)CH_3$ | H | H | 2 | $OCH_3$ | $N(CH_3)_2$ | |
| $CH_2CH_2OH$ | H | H | 2 | $CH_3$ | $N(CH_3)_2$ | |
| $C(O)CH_3$ | H | H | 2 | $OCH_3$ | $N(CH_3)_2$ | |
| $CH_2C(O)CH_3$ | H | H | 2 | $CH_3$ | $N(CH_3)_2$ | |
| $CHO$ | H | H | 2 | $OCH_3$ | $N(CH_3)_2$ | |
| $CH(OCH_3)_2$ | H | H | 2 | $CH_3$ | $N(CH_3)_2$ | |
| $OCH_2CH_2OCH_3$ | H | $CH_3$ | 2 | $CH_3$ | $CH_3$ | |
| $CO_2CH_3$ | H | $CH_3$ | 2 | $CH_3$ | $OCH_3$ | |
| $CO_2C_2H_5$ | H | $CH_3$ | 2 | $OCH_3$ | $OCH_3$ | |
| $CH_2CO_2CH_3$ | H | $CH_3$ | 2 | $CH_3$ | $CH_3$ | |
| $CN$ | H | $CH_3$ | 2 | $CH_3$ | $OCH_3$ | |
| $CH_2CN$ | H | $CH_3$ | 2 | $OCH_3$ | $OCH_3$ | |
| $CH_2OH$ | H | $CH_3$ | 2 | $CH_3$ | $CH_3$ | |
| $CH(OH)CH_3$ | H | $CH_3$ | 2 | $CH_3$ | $OCH_3$ | |
| $CH_2CH_2OH$ | H | $CH_3$ | 2 | $OCH_3$ | $OCH_3$ | |
| $CO_2CH_3$ | 5-$CH_3$ | H | 2 | $CH_3$ | $OCH_3$ | |
| $CO_2CH_3$ | 5-$CF_3$ | H | 2 | $OCH_3$ | $OCH_3$ | |
| $CO_2CH_3$ | 4-$CH_3$ | H | 2 | $CH_3$ | $CH_3$ | |
| $CO_2CH_3$ | 3-$CH_3$ | H | 2 | $CH_3$ | $OCH_3$ | |
| $CN$ | 5-$CH_3$ | H | 0 | $CH_3$ | $OCH_3$ | |
| $CN$ | 5-$CF_3$ | H | 0 | $OCH_3$ | $OCH_3$ | |
| $CH_2CH_2OH$ | 5-Cl | H | 2 | $OCH_3$ | $CH_3$ | |
| $CH_2CH_2OH$ | 4-$CH_3$ | H | 2 | $OCH_3$ | $OCH_3$ | |
| $CH_2CH_2OH$ | 5-$CH_3$ | H | 2 | $OCH_3$ | $CH_3$ | |
| $CH_2CH_2OH$ | 5-$CF_3$ | H | 2 | $OCH_3$ | $OCH_3$ | |
| $OCH_2CH_2OCH_3$ | H | H | 2 | Cl | $CH_3$ | |
| $CO_2CH_3$ | H | H | 2 | Cl | $CH_3$ | |
| $CH_2CO_2CH_3$ | H | H | 2 | Cl | $CH_3$ | |
| $CN$ | H | H | 2 | Cl | $CH_3$ | |
| $CH_2CN$ | H | H | 2 | Cl | $CH_3$ | |
| $CH_2CH_2OH$ | H | H | 2 | Cl | $CH_3$ | |
| $CO_2C_2H_5$ | H | H | 2 | Cl | $CH_2OCH_3$ | |
| $CH_2OH$ | H | H | 2 | Cl | $CH_2OCH_3$ | |
| $CO_2CH_3$ | H | H | 2 | Cl | $OCH_3$ | |
| $CO_2C_2H_5$ | H | H | 2 | Cl | $OCH_3$ | |
| $CN$ | H | H | 2 | Cl | $OCH_3$ | |
| $CH_2CN$ | H | H | 2 | Cl | $OCH_3$ | |
| $CH(OH)CH_3$ | H | H | 2 | Cl | $OCH_3$ | |
| $CH_2CH_2OH$ | H | H | 2 | Cl | $OCH_3$ | |
| $C(O)CH_3$ | H | H | 2 | Cl | $OCH_3$ | |
| $CHO$ | H | H | 2 | Cl | $OCH_3$ | |
| $CH(OCH_3)_2$ | H | H | 2 | Cl | $OCH_3$ | |
| $CO_2CH_3$ | H | H | 2 | Cl | $C_2H_5$ | |
| $CN$ | H | H | 2 | Cl | $C_2H_5$ | |
| $CH_2CN$ | H | H | 2 | Cl | $C_2H_5$ | |
| $CH_2CH_2OH$ | H | H | 2 | Cl | $C_2H_5$ | |
| $CO_2CH_3$ | H | H | 2 | Cl | $OC_2H_5$ | |
| $CN$ | H | H | 2 | Cl | $OC_2H_5$ | |
| $CH_2C(O)CH_3$ | H | H | 2 | Cl | $OC_2H_5$ | |
| $CHO$ | H | H | 2 | Cl | $OC_2H_5$ | |

TABLE I-continued

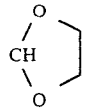

| A | R₁ | R₂ | n | X | Y | m.p. (°C.) |
|---|----|----|---|---|---|------------|
| ![dioxolane] CH(O-CH₂-CH₂-O) | H | H | 2 | Cl | OC₂H₅ | |
| OCH₃ | H | H | 2 | Cl | NH₂ | |
| OC₂H₅ | H | H | 2 | Cl | NHCH₃ | |
| CH₂OCH₃ | H | H | 2 | Cl | N(CH₃)₂ | |
| CH₂OC₂H₅ | H | H | 2 | Cl | NH₂ | |
| SO₂CH₃ | H | H | 2 | Cl | NHCH₃ | |
| CH₂SO₂CH₃ | H | H | 2 | Cl | N(CH₃)₂ | |

TABLE II

| A | R₁ | R₂ | n | X | Y | m.p. (°C.) |
|---|----|----|---|---|---|------------|
| OCH₃ | H | H | 0 | CH₃ | CH₃ | |
| OCH₃ | H | H | 0 | CH₃ | OCH₃ | |
| OCH₃ | H | H | 0 | OCH₃ | OCH₃ | |
| OCH₃ | H | H | 1 | CH₃ | CH₃ | |
| OCH₃ | H | H | 1 | CH₃ | OCH₃ | |
| OCH₃ | H | H | 1 | OCH₃ | OCH₃ | |
| OCH₃ | H | H | 2 | CH₃ | CH₃ | |
| OCH₃ | H | H | 2 | CH₃ | OCH₃ | |
| OCH₃ | H | H | 2 | OCH₃ | OCH₃ | |
| OC₂H₅ | H | H | 0 | CH₃ | CH₃ | |
| OC₂H₅ | H | H | 0 | CH₃ | OCH₃ | |
| OC₂H₅ | H | H | 0 | OCH₃ | OCH₃ | |
| OC₂H₅ | H | H | 1 | CH₃ | CH₃ | |
| OC₂H₅ | H | H | 1 | CH₃ | OCH₃ | |
| OC₂H₅ | H | H | 1 | OCH₃ | OCH₃ | |
| OC₂H₅ | H | H | 2 | CH₃ | CH₃ | |
| OC₂H₅ | H | H | 2 | CH₃ | OCH₃ | |
| OC₂H₅ | H | H | 2 | OCH₃ | OCH₃ | |
| CH₂OCH₃ | H | H | 0 | CH₃ | CH₃ | 139–142° |
| CH₂OCH₃ | H | H | 0 | CH₃ | OCH₃ | 131–133° |
| CH₂OCH₃ | H | H | 0 | OCH₃ | OCH₃ | 110–114° |
| CH₂OCH₃ | H | H | 1 | CH₃ | CH₃ | |
| CH₂OCH₃ | H | H | 1 | CH₃ | OCH₃ | |
| CH₂OCH₃ | H | H | 1 | OCH₃ | OCH₃ | |
| CH₂OCH₃ | H | H | 2 | CH₃ | CH₃ | 181–182° |
| CH₂OCH₃ | H | H | 2 | CH₃ | OCH₃ | 152–157° |
| CH₂OCH₃ | H | H | 2 | OCH₃ | OCH₃ | 158–163° |
| CH₂OC₂H₅ | H | H | 0 | CH₃ | CH₃ | |
| CH₂OC₂H₅ | H | H | 0 | CH₃ | OCH₃ | |
| CH₂OC₂H₅ | H | H | 0 | OCH₃ | OCH₃ | |
| CH₂OC₂H₅ | H | H | 1 | CH₃ | CH₃ | |
| CH₂OC₂H₅ | H | H | 1 | CH₃ | OCH₃ | |
| CH₂OC₂H₅ | H | H | 1 | OCH₃ | OCH₃ | |
| CH₂OC₂H₅ | H | H | 2 | CH₃ | CH₃ | |
| CH₂OC₂H₅ | H | H | 2 | CH₃ | OCH₃ | |
| CH₂OC₂H₅ | H | H | 2 | OCH₃ | OCH₃ | |
| OCH₂CH₂OCH₃ | H | H | 0 | CH₃ | CH₃ | |
| OCH₂CH₂OCH₃ | H | H | 0 | CH₃ | OCH₃ | |
| OCH₂CH₂OCH₃ | H | H | 0 | OCH₃ | OCH₃ | |
| OCH₂CH₂OCH₃ | H | H | 1 | CH₃ | CH₃ | |
| OCH₂CH₂OCH₃ | H | H | 1 | CH₃ | OCH₃ | |
| OCH₂CH₂OCH₃ | H | H | 1 | OCH₃ | OCH₃ | |
| OCH₂CH₂OCH₃ | H | H | 2 | CH₃ | CH₃ | |
| OCH₂CH₂OCH₃ | H | H | 2 | CH₃ | OCH₃ | |
| OCH₂CH₂OCH₃ | H | H | 2 | OCH₃ | OCH₃ | |

TABLE II-continued $$\underset{R_1}{\underset{|}{\text{C}_6\text{H}_3}}\text{(S(O)}_n\text{CH(R}_2\text{)A)}\text{--SO}_2\text{NHCONH--}\underset{Y}{\overset{X}{\text{C}_4\text{N}_3}}$$

| A | R₁ | R₂ | n | X | Y | m.p. (°C.) |
|---|----|----|---|---|---|------------|
| CH₂OCH₂CH₂OCH₃ | H | H | 0 | CH₃ | CH₃ | |
| CH₂OCH₂CH₂OCH₃ | H | H | 0 | CH₃ | OCH₃ | |
| CH₂OCH₂CH₂OCH₃ | H | H | 0 | OCH₃ | OCH₃ | |
| CH₂OCH₂CH₂OCH₃ | H | H | 1 | CH₃ | CH₃ | |
| CH₂OCH₂CH₂OCH₃ | H | H | 1 | CH₃ | OCH₃ | |
| CH₂OCH₂CH₂OCH₃ | H | H | 1 | OCH₃ | OCH₃ | |
| CH₂OCH₂CH₂OCH₃ | H | H | 2 | CH₃ | CH₃ | |
| CH₂OCH₂CH₂OCH₃ | H | H | 2 | CH₃ | OCH₃ | |
| CH₂OCH₂CH₂OCH₃ | H | H | 2 | OCH₃ | OCH₃ | |
| SCH₃ | H | H | 0 | CH₃ | CH₃ | |
| SCH₃ | H | H | 0 | CH₃ | OCH₃ | |
| SCH₃ | H | H | 0 | OCH₃ | OCH₃ | |
| SOCH₃ | H | H | 1 | CH₃ | CH₃ | |
| SOCH₃ | H | H | 1 | CH₃ | OCH₃ | |
| SOCH₃ | H | H | 1 | OCH₃ | OCH₃ | |
| SO₂CH₃ | H | H | 2 | CH₃ | CH₃ | |
| SO₂CH₃ | H | H | 2 | CH₃ | OCH₃ | |
| SO₂CH₃ | H | H | 2 | OCH₃ | OCH₃ | |
| SC₂H₅ | H | H | 0 | CH₃ | CH₃ | |
| SC₂H₅ | H | H | 0 | CH₃ | OCH₃ | |
| SC₂H₅ | H | H | 0 | OCH₃ | OCH₃ | |
| SOC₂H₅ | H | H | 1 | CH₃ | CH₃ | |
| SOC₂H₅ | H | H | 1 | CH₃ | OCH₃ | |
| SOC₂H₅ | H | H | 1 | OCH₃ | OCH₃ | |
| SO₂C₂H₅ | H | H | 2 | CH₃ | CH₃ | |
| SO₂C₂H₅ | H | H | 2 | CH₃ | OCH₃ | |
| SO₂C₂H₅ | H | H | 2 | OCH₃ | OCH₃ | |
| SCH₃ | H | H | 2 | CH₃ | CH₃ | |
| SCH₃ | H | H | 2 | CH₃ | OCH₃ | |
| SCH₃ | H | H | 2 | OCH₃ | OCH₃ | |
| SOCH₃ | H | H | 2 | CH₃ | CH₃ | |
| SOCH₃ | H | H | 2 | CH₃ | OCH₃ | |
| SOCH₃ | H | H | 2 | OCH₃ | OCH₃ | |
| CH₂SCH₃ | H | H | 0 | CH₃ | CH₃ | |
| CH₂SCH₃ | H | H | 0 | CH₃ | OCH₃ | |
| CH₂SCH₃ | H | H | 0 | OCH₃ | OCH₃ | |
| CH₂SOCH₃ | H | H | 1 | CH₃ | CH₃ | |
| CH₂SOCH₃ | H | H | 1 | CH₃ | OCH₃ | |
| CH₂SOCH₃ | H | H | 1 | OCH₃ | OCH₃ | |
| CH₂SO₂CH₃ | H | H | 2 | CH₃ | CH₃ | |
| CH₂SO₂CH₃ | H | H | 2 | CH₃ | OCH₃ | |
| CH₂SO₂CH₃ | H | H | 2 | OCH₃ | OCH₃ | |
| CH₂SC₂H₅ | H | H | 0 | CH₃ | CH₃ | |
| CH₂SC₂H₅ | H | H | 0 | CH₃ | OCH₃ | |
| CH₂SC₂H₅ | H | H | 0 | OCH₃ | OCH₃ | |
| CH₂SOC₂H₅ | H | H | 1 | CH₃ | CH₃ | |
| CH₂SOC₂H₅ | H | H | 1 | CH₃ | OCH₃ | |
| CH₂SOC₂H₅ | H | H | 1 | OCH₃ | OCH₃ | |
| CH₂SO₂C₂H₅ | H | H | 2 | CH₃ | CH₃ | |
| CH₂SO₂C₂H₅ | H | H | 2 | CH₃ | OCH₃ | |
| CH₂SO₂C₂H₅ | H | H | 2 | OCH₃ | OCH₃ | |
| CO₂CH₃ | H | H | 0 | CH₃ | CH₃ | |
| CO₂CH₃ | H | H | 0 | CH₃ | OCH₃ | 140–145° |
| CO₂CH₃ | H | H | 0 | OCH₃ | OCH₃ | |
| CO₂CH₃ | H | H | 1 | CH₃ | CH₃ | |
| CO₂CH₃ | H | H | 1 | CH₃ | OCH₃ | |
| CO₂CH₃ | H | H | 1 | OCH₃ | OCH₃ | |
| CO₂CH₃ | H | H | 2 | CH₃ | CH₃ | |
| CO₂CH₃ | H | H | 2 | CH₃ | OCH₃ | 74–77° |
| CO₂CH₃ | H | H | 2 | OCH₃ | OCH₃ | |
| CO₂C₂H₅ | H | H | 0 | CH₃ | CH₃ | |
| CO₂C₂H₅ | H | H | 0 | CH₃ | OCH₃ | |
| CO₂C₂H₅ | H | H | 0 | OCH₃ | OCH₃ | |
| CO₂C₂H₅ | H | H | 1 | CH₃ | CH₃ | |
| CO₂C₂H₅ | H | H | 1 | CH₃ | OCH₃ | |
| CO₂C₂H₅ | H | H | 1 | OCH₃ | OCH₃ | |
| CO₂C₂H₅ | H | H | 2 | CH₃ | CH₃ | |
| CO₂C₂H₅ | H | H | 2 | CH₃ | OCH₃ | |
| CO₂C₂H₅ | H | H | 2 | OCH₃ | OCH₃ | |
| CH₂CO₂CH₃ | H | H | 0 | CH₃ | CH₃ | |
| CH₂CO₂CH₃ | H | H | 0 | CH₃ | OCH₃ | |
| CH₂CO₂CH₃ | H | H | 0 | OCH₃ | OCH₃ | |

TABLE II-continued

[Structure: benzene ring with substituents S(O)ₙCH(R₂)A, R₁, and SO₂NHCONH-triazine with X and Y]

| A | R₁ | R₂ | n | X | Y | m.p. (°C.) |
|---|----|----|----|---|---|-----------|
| CH₂CO₂CH₃ | H | H | 1 | CH₃ | CH₃ | |
| CH₂CO₂CH₃ | H | H | 1 | CH₃ | OCH₃ | |
| CH₂CO₂CH₃ | H | H | 1 | OCH₃ | OCH₃ | |
| CH₂CO₂CH₃ | H | H | 2 | CH₃ | CH₃ | |
| CH₂CO₂CH₃ | H | H | 2 | CH₃ | OCH₃ | |
| CH₂CO₂CH₃ | H | H | 2 | OCH₃ | OCH₃ | |
| CH₂CO₂C₂H₅ | H | H | 0 | CH₃ | CH₃ | |
| CH₂CO₂C₂H₅ | H | H | 0 | CH₃ | OCH₃ | |
| CH₂CO₂C₂H₅ | H | H | 0 | OCH₃ | OCH₃ | |
| CH₂CO₂C₂H₅ | H | H | 1 | CH₃ | CH₃ | |
| CH₂CO₂C₂H₅ | H | H | 1 | CH₃ | OCH₃ | |
| CH₂CO₂C₂H₅ | H | H | 1 | OCH₃ | OCH₃ | |
| CH₂CO₂C₂H₅ | H | H | 2 | CH₃ | CH₃ | |
| CH₂CO₂C₂H₅ | H | H | 2 | CH₃ | OCH₃ | |
| CH₂CO₂C₂H₅ | H | H | 2 | OCH₃ | OCH₃ | |
| CN | H | H | 0 | CH₃ | CH₃ | 200–201° |
| CN | H | H | 0 | CH₃ | OCH₃ | 187–189° |
| CN | H | H | 0 | OCH₃ | OCH₃ | 183–185° |
| CN | H | H | 1 | CH₃ | CH₃ | |
| CN | H | H | 1 | CH₃ | OCH₃ | 163–168° (D) |
| CN | H | H | 1 | OCH₃ | OCH₃ | 172–176° (D) |
| CN | H | H | 2 | CH₃ | CH₃ | 90–126° |
| CN | H | H | 2 | CH₃ | OCH₃ | 180–184° |
| CN | H | H | 2 | OCH₃ | OCH₃ | >280° |
| CH₂CN | H | H | 0 | CH₃ | CH₃ | |
| CH₂CN | H | H | 0 | CH₃ | OCH₃ | |
| CH₂CN | H | H | 0 | OCH₃ | OCH₃ | |
| CH₂CN | H | H | 1 | CH₃ | CH₃ | |
| CH₂CN | H | H | 1 | CH₃ | OCH₃ | |
| CH₂CN | H | H | 1 | OCH₃ | OCH₃ | |
| CH₂CN | H | H | 2 | CH₃ | CH₃ | |
| CH₂CN | H | H | 2 | CH₃ | OCH₃ | |
| CH₂CN | H | H | 2 | OCH₃ | OCH₃ | |
| 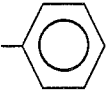 | H | H | 0 | CH₃ | CH₃ | |
| 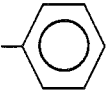 | H | H | 0 | CH₃ | OCH₃ | |
| 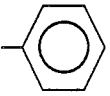 | H | H | 0 | OCH₃ | OCH₃ | |
| 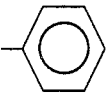 | H | H | 1 | CH₃ | CH₃ | |
| 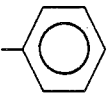 | H | H | 1 | CH₃ | OCH₃ | |
| 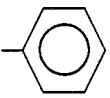 | H | H | 1 | OCH₃ | OCH₃ | |

TABLE II-continued
|  | | | | | | |
|---|---|---|---|---|---|---|
| A | R₁ | R₂ | n | X | Y | m.p. (°C.) |
| 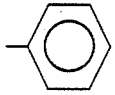 | H | H | 2 | CH₃ | CH₃ | 144–151° |
| 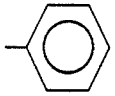 | H | H | 2 | CH₃ | OCH₃ | 157–170° |
| 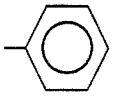 | H | H | 2 | OCH₃ | OCH₃ | 157–164° |
| 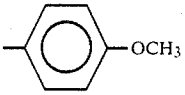 | H | H | 0 | CH₃ | CH₃ | |
| 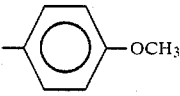 | H | H | 0 | CH₃ | OCH₃ | |
| 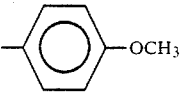 | H | H | 0 | OCH₃ | OCH₃ | |
| 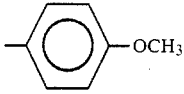 | H | H | 1 | CH₃ | CH₃ | |
| 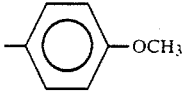 | H | H | 1 | CH₃ | OCH₃ | |
| 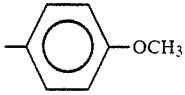 | H | H | 1 | OCH₃ | OCH₃ | |
| 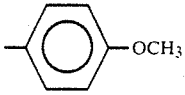 | H | H | 2 | CH₃ | CH₃ | 195–198° |
| 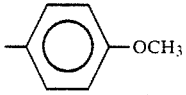 | H | H | 2 | CH₃ | OCH₃ | 125–129° |
| 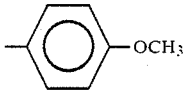 | H | H | 2 | OCH₃ | OCH₃ | 120–122° |

TABLE II-continued
[Structure: phenyl ring with S(O)ₙCH(R₂)A group, SO₂NHCONH— linked to triazine ring with X and Y substituents, R₁ on phenyl]
| A | R₁ | R₂ | n | X | Y | m.p. (°C.) |
|---|----|----|----|----|----|----|
| 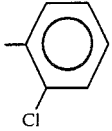 | H | H | 0 | CH₃ | CH₃ | |
| 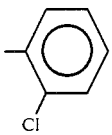 | H | H | 0 | CH₃ | OCH₃ | |
| 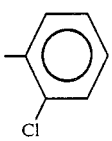 | H | H | 0 | OCH₃ | OCH₃ | |
| 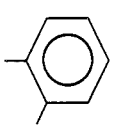 | H | H | 2 | CH₃ | CH₃ | |
| 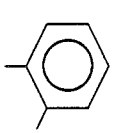 | H | H | 2 | CH₃ | OCH₃ | |
| 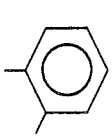 | H | H | 2 | OCH₃ | OCH₃ | |
| 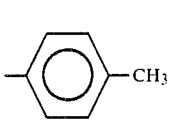 | H | H | 2 | CH₃ | CH₃ | |
| 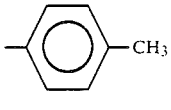 | H | H | 2 | CH₃ | OCH₃ | |
| 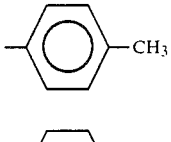 | H | H | 2 | OCH₃ | OCH₃ | |
| 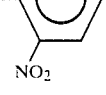 | H | H | 2 | CH₃ | CH₃ | |

TABLE II-continued
![structure](chemical structure: R1-phenyl with S(O)nCH(R2)A and SO2NHCONH-triazine with X and Y)
| A | R1 | R2 | n | X | Y | m.p. (°C.) |
|---|---|---|---|---|---|---|
| 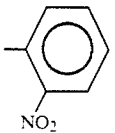 (2-NO2-phenyl) | H | H | 2 | CH3 | OCH3 | |
| 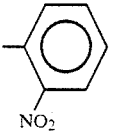 (2-NO2-phenyl) | H | H | 2 | OCH3 | OCH3 | |
| 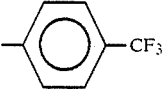 (4-CF3-phenyl) | H | H | 2 | CH3 | CH3 | |
| 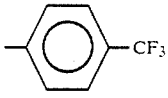 (4-CF3-phenyl) | H | H | 2 | CH3 | OCH3 | |
| 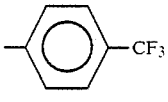 (4-CF3-phenyl) | H | H | 2 | OCH3 | OCH3 | |
| 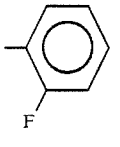 (2-F-phenyl) | H | H | 2 | CH3 | CH3 | |
| 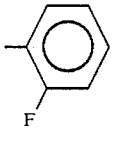 (2-F-phenyl) | H | H | 2 | CH3 | OCH3 | |
| 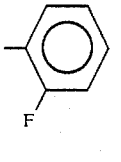 (2-F-phenyl) | H | H | 2 | OCH3 | OCH3 | |
| 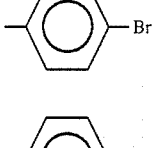 (4-Br-phenyl) | H | H | 2 | CH3 | CH3 | |
| 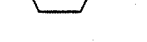 (4-Br-phenyl) | H | H | 2 | CH3 | OCH3 | |

TABLE II-continued
| A | R₁ | R₂ | n | X | Y | m.p. (°C.) |
|---|---|---|---|---|---|---|
| 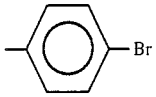 4-Br-phenyl | H | H | 2 | OCH₃ | OCH₃ | |
| 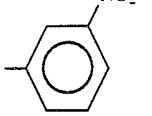 3-NO₂-phenyl | H | H | 0 | CH₃ | CH₃ | |
| 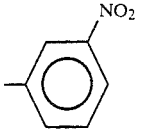 3-NO₂-phenyl | H | H | 0 | CH₃ | OCH₃ | |
| 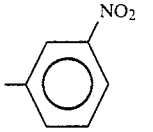 3-NO₂-phenyl | H | H | 0 | OCH₃ | OCH₃ | |
| 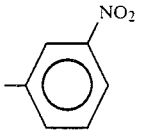 3-NO₂-phenyl | H | H | 2 | CH₃ | CH₃ | |
| 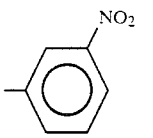 3-NO₂-phenyl | H | H | 2 | CH₃ | OCH₃ | |
| 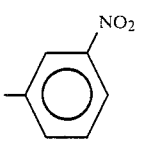 3-NO₂-phenyl | H | H | 2 | OCH₃ | OCH₃ | |
| 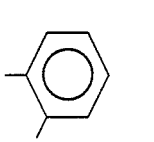 3-OCH₃-phenyl | H | H | 2 | CH₃ | CH₃ | |
| 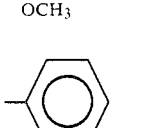 3-OCH₃-phenyl | H | H | 2 | CH₃ | OCH₃ | |
| 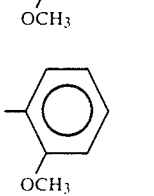 3-OCH₃-phenyl | H | H | 2 | OCH₃ | OCH₃ | |

TABLE II-continued

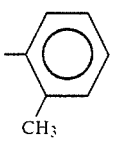

| A | R₁ | R₂ | n | X | Y | m.p. (°C.) |
|---|---|---|---|---|---|---|
| 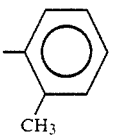 (2-CH₃-phenyl) | 5-F | CH₃ | 2 | CH₃ | CH₃ | |
| 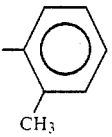 (2-CH₃-phenyl) | 5-Cl | CH₃ | 2 | CH₃ | OCH₃ | |
| 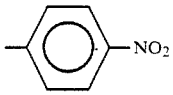 (2-CH₃-phenyl) | 5-Br | CH₃ | 2 | OCH₃ | OCH₃ | |
| CH₂OCH₃ | 5-CH₃ | CH₃ | 2 | CH₃ | C₂H₅ | |
| CH₂OCH₃ | 5-OCH₃ | CH₃ | 2 | CH₃ | CH₂OCH₃ | |
| CH₂OCH₃ | 5-CF₃ | CH₃ | 2 | CH₃ | OC₂H₅ | |
| CH₂OCH₃ | 5-NO₂ | CH₃ | 2 | OCH₃ | CH₃ | |
| CH₂OCH₃ | 4-CH₃ | CH₃ | 2 | CH₃ | CH₃ | |
| CH₂OCH₃ | 4-OCH₃ | CH₃ | 2 | OCH₃ | OC₂H₅ | |
| OCH₃ | 6-Cl | CH₃ | 0 | OCH₃ | CH₂OCH₃ | |
| OCH₃ | 6-CH₃ | CH₃ | 1 | OCH₃ | OCH₃ | |
| CO₂CH₃ | 3-Br | CH₃ | 2 | OCH₃ | CH₃ | |
| CH₂CO₂C₂H₅ | 5-CH₃ | CH₃ | 2 | CH₃ | CH₂OCH₃ | |
| SO₂CH₃ | 5-CF₃ | CH₃ | 2 | CH₃ | OC₂H₅ | |
| CH₂SO₂CH₃ | 5-Cl | CH₃ | 2 | OCH₃ | OCH₃ | |
| CN | 5-CF₃ | CH₃ | 2 | OCH₃ | OCH₃ | |
| CH₂CN | 5-NO₂ | CH₃ | 2 | CH₃ | CH₃ | |
| 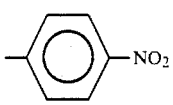 (4-NO₂-phenyl) | H | H | 2 | CH₃ | CH₃ | |
| 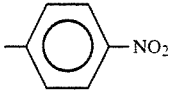 (4-NO₂-phenyl) | H | H | 2 | CH₃ | OCH₃ | |
| 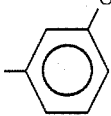 (4-NO₂-phenyl) | H | H | 2 | OCH₃ | OCH₃ | |
| 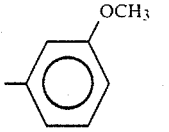 (2-OCH₃-phenyl) | H | H | 2 | CH₃ | CH₃ | |
| 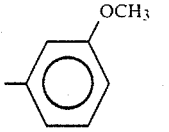 (2-OCH₃-phenyl) | H | H | 2 | CH₃ | OCH₃ | |

TABLE II-continued

Structure: Benzene ring with S(O)ₙCH(R₂)A and SO₂NHCONH-[pyrimidine with X, Y substituents], and R₁ on the ring.

| A | R₁ | R₂ | n | X | Y | m.p. (°C.) |
|---|----|----|---|---|---|------------|
| 3-methoxyphenyl | H | H | 2 | OCH₃ | OCH₃ | |
| 3-methylphenyl | H | H | 2 | CH₃ | CH₃ | |
| 3-methylphenyl | H | H | 2 | CH₃ | OCH₃ | |
| 3-methylphenyl | H | H | 2 | OCH₃ | OCH₃ | |
| 3-chlorophenyl | H | H | 2 | CH₃ | CH₃ | |
| 3-chlorophenyl | H | H | 2 | CH₃ | OCH₃ | |
| 3-chlorophenyl | H | H | 2 | OCH₃ | OCH₃ | |
| CH₂OH | H | H | 0 | CH₃ | CH₃ | |
| CH₂OH | H | H | 0 | CH₃ | OCH₃ | |
| CH₂OH | H | H | 0 | OCH₃ | OCH₃ | |
| CH₂OH | H | H | 1 | CH₃ | CH₃ | |
| CH₂OH | H | H | 1 | CH₃ | OCH₃ | |
| CH₂OH | H | H | 1 | OCH₃ | OCH₃ | |
| CH₂OH | H | H | 2 | CH₃ | CH₃ | |
| CH₂OH | H | H | 2 | CH₃ | OCH₃ | |
| CH₂OH | H | H | 2 | OCH₃ | OCH₃ | |
| CH(OH)CH₃ | H | H | 0 | CH₃ | CH₃ | |
| CH(OH)CH₃ | H | H | 0 | CH₃ | OCH₃ | |
| CH(OH)CH₃ | H | H | 0 | OCH₃ | OCH₃ | |
| CH(OH)CH₃ | H | H | 1 | CH₃ | CH₃ | |
| CH(OH)CH₃ | H | H | 1 | CH₃ | OCH₃ | |
| CH(OH)CH₃ | H | H | 1 | OCH₃ | OCH₃ | |
| CH(OH)CH₃ | H | H | 2 | CH₃ | CH₃ | |
| CH(OH)CH₃ | H | H | 2 | CH₃ | OCH₃ | |
| CH(OH)CH₃ | H | H | 2 | OCH₃ | OCH₃ | |
| CH₂CH₂OH | H | H | 0 | CH₃ | CH₃ | |
| CH₂CH₂OH | H | H | 0 | CH₃ | OCH₃ | |
| CH₂CH₂OH | H | H | 0 | OCH₃ | OCH₃ | |

TABLE II-continued $$\underset{R_1}{\text{[benzene ring with substituents: }S(O)_nCH(R_2)A\text{ and }SO_2NHCONH\text{-pyrimidine with X, Y, }R_1]}$$

| A | $R_1$ | $R_2$ | n | X | Y | m.p. (°C.) |
|---|---|---|---|---|---|---|
| CH$_2$CH$_2$OH | H | H | 1 | CH$_3$ | CH$_3$ | |
| CH$_2$CH$_2$OH | H | H | 1 | CH$_3$ | OCH$_3$ | |
| CH$_2$CH$_2$OH | H | H | 1 | OCH$_3$ | OCH$_3$ | |
| CH$_2$CH$_2$OH | H | H | 2 | CH$_3$ | CH$_3$ | |
| CH$_2$CH$_2$OH | H | H | 2 | CH$_3$ | OCH$_3$ | |
| CH$_2$CH$_2$OH | H | H | 2 | OCH$_3$ | OCH$_3$ | |
| C(O)CH$_3$ | H | H | 0 | CH$_3$ | CH$_3$ | |
| C(O)CH$_3$ | H | H | 0 | CH$_3$ | OCH$_3$ | |
| C(O)CH$_3$ | H | H | 0 | OCH$_3$ | OCH$_3$ | |
| C(O)CH$_3$ | H | H | 1 | CH$_3$ | CH$_3$ | |
| C(O)CH$_3$ | H | H | 1 | CH$_3$ | OCH$_3$ | |
| C(O)CH$_3$ | H | H | 1 | OCH$_3$ | OCH$_3$ | |
| C(O)CH$_3$ | H | H | 2 | CH$_3$ | CH$_3$ | |
| C(O)CH$_3$ | H | H | 2 | CH$_3$ | OCH$_3$ | |
| C(O)CH$_3$ | H | H | 2 | OCH$_3$ | OCH$_3$ | |
| CH$_2$C(O)CH$_3$ | H | H | 0 | CH$_3$ | CH$_3$ | |
| CH$_2$C(O)CH$_3$ | H | H | 0 | CH$_3$ | OCH$_3$ | |
| CH$_2$C(O)CH$_3$ | H | H | 0 | OCH$_3$ | OCH$_3$ | |
| CH$_2$C(O)CH$_3$ | H | H | 1 | CH$_3$ | CH$_3$ | |
| CH$_2$C(O)CH$_3$ | H | H | 1 | CH$_3$ | OCH$_3$ | |
| CH$_2$C(O)CH$_3$ | H | H | 1 | OCH$_3$ | OCH$_3$ | |
| CH$_2$C(O)CH$_3$ | H | H | 2 | CH$_3$ | CH$_3$ | |
| CH$_2$C(O)CH$_3$ | H | H | 2 | CH$_3$ | OCH$_3$ | |
| CH$_2$C(O)CH$_3$ | H | H | 2 | OCH$_3$ | OCH$_3$ | |
| CHO | H | H | 0 | CH$_3$ | CH$_3$ | |
| CHO | H | H | 0 | CH$_3$ | OCH$_3$ | |
| CHO | H | H | 0 | OCH$_3$ | OCH$_3$ | |
| CHO | H | H | 1 | CH$_3$ | CH$_3$ | |
| CHO | H | H | 1 | CH$_3$ | OCH$_3$ | |
| CHO | H | H | 1 | OCH$_3$ | OCH$_3$ | |
| CHO | H | H | 2 | CH$_3$ | CH$_3$ | |
| CHO | H | H | 2 | CH$_3$ | OCH$_3$ | |
| CHO | H | H | 2 | OCH$_3$ | OCH$_3$ | |
| CH(OCH$_3$)$_2$ | H | H | 0 | CH$_3$ | CH$_3$ | |
| CH(OCH$_3$)$_2$ | H | H | 0 | CH$_3$ | OCH$_3$ | |
| CH(OCH$_3$)$_2$ | H | H | 0 | OCH$_3$ | OCH$_3$ | |
| CH(OCH$_3$)$_2$ | H | H | 1 | CH$_3$ | CH$_3$ | |
| CH(OCH$_3$)$_2$ | H | H | 1 | CH$_3$ | OCH$_3$ | |
| CH(OCH$_3$)$_2$ | H | H | 1 | OCH$_3$ | OCH$_3$ | |
| CH(OCH$_3$)$_2$ | H | H | 2 | CH$_3$ | CH$_3$ | |
| CH(OCH$_3$)$_2$ | H | H | 2 | CH$_3$ | OCH$_3$ | |
| CH(OCH$_3$)$_2$ | H | H | 2 | OCH$_3$ | OCH$_3$ | |
| 1,3-dioxolan-2-yl | H | H | 0 | CH$_3$ | CH$_3$ | |
| 1,3-dioxolan-2-yl | H | H | 0 | CH$_3$ | OCH$_3$ | |
| 1,3-dioxolan-2-yl | H | H | 0 | OCH$_3$ | OCH$_3$ | |
| 1,3-dioxolan-2-yl | H | H | 1 | CH$_3$ | CH$_3$ | |
| 1,3-dioxolan-2-yl | H | H | 1 | CH$_3$ | OCH$_3$ | |

TABLE II-continued

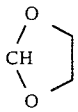

| A | R₁ | R₂ | n | X | Y | m.p. (°C.) |
|---|----|----|---|---|---|-----------|
| $\begin{array}{c} O \\ / \\ CH \\ \backslash \\ O \end{array}\Big\}$ | H | H | 1 | OCH₃ | OCH₃ | |
| $\begin{array}{c} O \\ / \\ CH \\ \backslash \\ O \end{array}\Big\}$ | H | H | 2 | CH₃ | CH₃ | |
| $\begin{array}{c} O \\ / \\ CH \\ \backslash \\ O \end{array}\Big\}$ | H | H | 2 | CH₃ | OCH₃ | |
| $\begin{array}{c} O \\ / \\ CH \\ \backslash \\ O \end{array}\Big\}$ | H | H | 2 | OCH₃ | OCH₃ | |
| OCH₃ | H | H | 2 | CH₃ | NH₂ | |
| CH₂OCH₃ | H | H | 2 | OCH₃ | NH₂ | |
| OCH₂CH₂OCH₃ | H | H | 2 | CH₃ | NH₂ | |
| CH₂OCH₂CH₂OCH₃ | H | H | 2 | OCH₃ | NH₂ | |
| SO₂CH₃ | H | H | 2 | CH₃ | NH₂ | |
| CH₂SO₂CH₃ | H | H | 2 | OCH₃ | NH₂ | |
| CO₂CH₃ | H | H | 2 | CH₃ | NH₂ | |
| CH₂CO₂CH₃ | H | H | 2 | OCH₃ | NH₂ | |
| CN | H | H | 2 | CH₃ | NH₂ | |
| CH₂CN | H | H | 2 | OCH₃ | NH₂ | |
| CH₂OH | H | H | 2 | CH₃ | NH₂ | |
| CH(OH)CH₃ | H | H | 2 | OCH₃ | NH₂ | |
| CH₂CH₂OH | H | H | 2 | CH₃ | NH₂ | |
| C(O)CH₃ | H | H | 2 | OCH₃ | NH₂ | |
| CH₂C(O)CH₃ | H | H | 2 | CH₃ | NH₂ | |
| CHO | H | H | 2 | OCH₃ | NH₂ | |
| CH(OCH₃)₂ | H | H | 2 | CH₃ | NH₂ | |
| OCH₃ | H | H | 2 | CH₃ | NHCH₃ | |
| CH₂OCH₃ | H | H | 2 | OCH₃ | NHCH₃ | |
| OCH₂CH₂OCH₃ | H | H | 2 | CH₃ | NHCH₃ | |
| CH₂OCH₂CH₂OCH₃ | H | H | 2 | OCH₃ | NHCH₃ | |
| SO₂CH₃ | H | H | 2 | CH₃ | NHCH₃ | |
| CH₂SO₂CH₃ | H | H | 2 | OCH₃ | NHCH₃ | |
| CO₂CH₃ | H | H | 2 | CH₃ | NHCH₃ | |
| CH₂CO₂CH₃ | H | H | 2 | OCH₃ | NHCH₃ | |
| CN | H | H | 2 | CH₃ | NHCH₃ | |
| CH₂CN | H | H | 2 | OCH₃ | NHCH₃ | |
| CH₂OH | H | H | 2 | CH₃ | NHCH₃ | |
| CH(OH)CH₃ | H | H | 2 | OCH₃ | NHCH₃ | |
| CH₂CH₂OH | H | H | 2 | CH₃ | NHCH₃ | |
| C(O)CH₃ | H | H | 2 | OCH₃ | NHCH₃ | |
| CH₂C(O)CH₃ | H | H | 2 | CH₃ | NHCH₃ | |
| CHO | H | H | 2 | OCH₃ | NHCH₃ | |
| CH(OCH₃)₂ | H | H | 2 | CH₃ | NHCH₃ | |
| $\begin{array}{c} O \\ / \\ CH \\ \backslash \\ O \end{array}\Big\}$ | H | H | 2 | OCH₃ | NHCH₃ | |
| OCH₃ | H | H | 2 | CH₃ | N(CH₃)₂ | |
| CH₂OCH₃ | H | H | 2 | OCH₃ | N(CH₃)₂ | |
| OCH₂CH₂OCH₃ | H | H | 2 | CH₃ | N(CH₃)₂ | |
| CH₂OCH₂CH₂OCH₃ | H | H | 2 | OCH₃ | N(CH₃)₂ | |
| SO₂CH₃ | H | H | 2 | CH₃ | N(CH₃)₂ | |
| CH₂SO₂CH₃ | H | H | 2 | OCH₃ | N(CH₃)₂ | |

TABLE II-continued

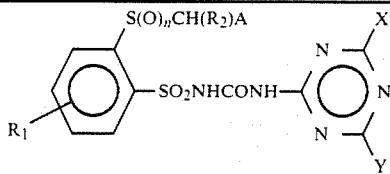

| A | $R_1$ | $R_2$ | n | X | Y | m.p. (°C.) |
|---|---|---|---|---|---|---|
| $CO_2CH_3$ | H | H | 2 | $CH_3$ | $N(CH_3)_2$ | |
| $CH_2CO_2CH_3$ | H | H | 2 | $OCH_3$ | $N(CH_3)_2$ | |
| CN | H | H | 2 | $CH_3$ | $N(CH_3)_2$ | |
| $CH_2CN$ | H | H | 2 | $OCH_3$ | $N(CH_3)_2$ | |
| $CH_2OH$ | H | H | 2 | $CH_3$ | $N(CH_3)_2$ | |
| $CH(OH)CH_3$ | H | H | 2 | $OCH_3$ | $N(CH_3)_2$ | |
| $CH_2CH_2OH$ | H | H | 2 | $CH_3$ | $N(CH_3)_2$ | |
| $C(O)CH_3$ | H | H | 2 | $OCH_3$ | $N(CH_3)_2$ | |
| $CH_2C(O)CH_3$ | H | H | 2 | $CH_3$ | $N(CH_3)_2$ | |
| CHO | H | H | 2 | $OCH_3$ | $N(CH_3)_2$ | |
| $CH(OCH_3)_2$ | H | H | 2 | $CH_3$ | $N(CH_3)_2$ | |
| $OCH_2CH_2OCH_3$ | H | $CH_3$ | 2 | $CH_3$ | $CH_3$ | |
| $CO_2CH_3$ | H | $CH_3$ | 2 | $CH_3$ | $OCH_3$ | |
| $CO_2C_2H_5$ | H | $CH_3$ | 2 | $OCH_3$ | $OCH_3$ | |
| $CH_2CO_2CH_3$ | H | $CH_3$ | 2 | $CH_3$ | $CH_3$ | |
| CN | H | $CH_3$ | 2 | $CH_3$ | $OCH_3$ | |
| $CH_2CN$ | H | $CH_3$ | 2 | $OCH_3$ | $OCH_3$ | |
| $CH_2OH$ | H | $CH_3$ | 2 | $CH_3$ | $CH_3$ | |
| $CH(OH)CH_3$ | H | $CH_3$ | 2 | $CH_3$ | $OCH_3$ | |
| $CH_2CH_2OH$ | H | $CH_3$ | 2 | $OCH_3$ | $OCH_3$ | |
| $CO_2CH_3$ | 5-$CH_3$ | H | 2 | $CH_3$ | $OCH_3$ | |
| $CO_2CH_3$ | 5-$CF_3$ | H | 2 | $OCH_3$ | $OCH_3$ | |
| $CO_2CH_3$ | 4-$CH_3$ | H | 2 | $CH_3$ | $CH_3$ | |
| $CO_2CH_3$ | 3-$CH_3$ | H | 2 | $CH_3$ | $OCH_3$ | |
| CN | 5-$CH_3$ | H | 0 | $CH_3$ | $OCH_3$ | |
| CN | 5-$CF_3$ | H | 0 | $OCH_3$ | $OCH_3$ | |
| $CH_2CH_2OH$ | 5-Cl | H | 2 | $OCH_3$ | $CH_3$ | |
| $CH_2CH_2OH$ | 4-$CH_3$ | H | 2 | $OCH_3$ | $OCH_3$ | |
| $CH_2CH_2OH$ | 5-$CH_3$ | H | 2 | $OCH_3$ | $CH_3$ | |
| $CH_2CH_2OH$ | 5-$CF_3$ | H | 2 | $OCH_3$ | $OCH_3$ | |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE III

| | Active Ingredient | Weight Percent* Diluent(s) | Surfactant(s) |
|---|---|---|---|
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138-140, 162-164, 166, 167 and 169-182;

H. Gysin and E. Knusli, U.S. Pat. No. 2,891,855, June 23, 1959, Col. 3, line 66 through Col. 5, line 17 and Examples 1-4;

G. C. Klingman, "Weed Control as a Science", John Wiley & Sons, Inc., New York, 1961, pp. 81-96; and J. D. Fryer and S. A. Evans, "Weed Control Handbook", 5th Ed., Blackwell Scientific Publications, Oxford, 1968, pp. 101-103.

In the following examples, all parts are by weight unless otherwise indicated.

EXAMPLE 7

| Wettable Powder | |
|---|---|
| N—[(4,6-dimethylpyrimidin-2-yl)aminocarbonyl]-2-(2-methoxyethylsulfonyl)benzenesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 8

| Wettable Powder | |
|---|---|
| 2-(2-methoxyethylsulfonyl)-N—[(4-methoxy-6-methyl-pyrimidin-2-yl)aminocarbonyl]benzenesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 9

| Granule | |
|---|---|
| Wettable Powder of Example 8 | 5% |
| attapulgite granules (U.S.S. 20-40 mesh: 0.84-0.42 mm) | 95% |

A slurry of wettable powder containing ≈25% solids is sprayed on the surface of attapulgite granules in a double-cone blender. The granules are dried and packaged.

EXAMPLE 10

| Extruded Pellet | |
|---|---|
| N—[(4,6-dimethoxypyrimidin-2-yl)aminocarbonyl]-2-(2-methoxyethylsulfonyl)benzenesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. Pat. No. 20 sieve (0.84 mm openings). The granules held on a U.S.S. No. 40 sieve (0.42 mm openings) may be packaged for use and the fines recycled.

EXAMPLE 11

| Oil Suspension | |
|---|---|
| N—[(4,6-dimethyl-1,3,5-triazin-2-yl)aminocarbonyl]-2-(2-methoxyethylsulfonyl)benzenesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 12

| Wettable Powder | |
|---|---|
| 2-(2-methoxyethylsulfonyl)-N—[(4-methoxy-6-methyl-1,3,5-triazin-2-yl)aminocarbonyl]benzenesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 13

| Low Strength Granule | |
|---|---|
| N—[(4,6-dimethoxypyrimidin-2-yl)aminocarbonyl]-2-(2-methoxyethylsulfonyl)benzenesulfonamide | 1% |
| N,N—dimethylformamide | 9% |
| attapulgite granules (U.S.S. 20-40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 14

| Aqueous Suspension | |
|---|---|
| N—[(4,6-dimethyl-1,3,5-triazin-2-yl)aminocarbonyl]-2-(2-methoxyethylsulfonyl)benzenesulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 15

| Solution | |
|---|---|
| 2-(2-methoxyethylsulfonyl)-N—[(4-methoxy-6-methyl-pyrimidin-2-yl)aminocarbonyl]benzenesulfonamide, sodium salt | 5% |
| water | 95% |

The salt is added directly to the water with stirring to produce the solution, which may then be packaged for use.

EXAMPLE 16

| Low Strength Granule | |
|---|---|
| N—[(4,6-dimethyl-1,3,5-triazin-2-yl)aminocarbonyl]-2-(2-methoxyethylsulfonyl)benzenesulfonamide | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 17

| Granule | |
|---|---|
| N—[(4,6-dimethoxypyrimidin-2-yl)aminocarbonyl]-2-(2-methoxyethylsulfonyl)benzenesulfonamide | 80% |
| wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 18

| High Strength Concentrate | |
|---|---|
| N—[(4,6-dimethylpyrimidin-2-yl)aminocarbonyl]-2-(2-methoxyethylsulfonyl)benzenesulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 19

| Wettable Powder | |
|---|---|
| N—[(4,6-dimethoxypyrimidin-2-yl)aminocarbonyl]-2-(2-methoxyethylsulfonyl)benzenesulfonamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 20

| Wettable Powder | |
|---|---|
| 2-(2-methoxyethylsulfonyl)-N—[(4-methoxy-6-methyl-1,3,5-triazin-2-yl)aminocarbonyl]benzenesulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 21

| Oil Suspension | |
|---|---|
| N—[(4,6-dimethylpyrimidin-2-yl)aminocarbonyl]-2-2-methoxyethylsulfonyl benzenesulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

UTILITY

The compounds of the present invention are active herbicides. They have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, the subject compounds are useful for the selective pre- or post-emergence weed control in crops, such as wheat and soybeans.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.05 to 10 kg/ha, the lower rates being suggested for use on lighter soils and/or those having a low organic matter content, for selective weed control or for situations where only short-term persistence is required.

The compounds of the invention may be used in combination with many other commercial herbicide examples of which are those of the triazine, triazole, uracil, urea, amide, diphenylether, carbamate and bipyridylium types.

The herbicidal properties of the subject compounds were discovered in a number of greenhouse tests. The test procedures and results follow.

TEST A

Seeds of crabgrass (*Digitaria sp.*), barnyardgrass (*Echinochloa crusgalli*), wild oats (*Avena fatua*), cassia (*Cassia tora*), morningglory (*Ipomoea sp.*), cocklebur (*Xanthium sp.*), sorghum, corn, soybean, rice, wheat and nutsedge tubers (*Cyperus rotundus*) were planted in a growth medium and treated pre-emergence with the chemicals dissolved in a non-phytotoxic solvent. At the same time, cotton having five leaves (including cotyledonary ones), bush beans with the third trifoliolate leaf expanding, crabgrass, barnyardgrass and wild oats with two leaves, cassia with three leaves (including cotyledonary ones), morningglory and cocklebur with four leaves (including the cotyledonary ones), sorghum and corn with four leaves, soybean with two cotyledonary leaves, rice with three leaves, wheat with one leaf, and nutsedge with three to five leaves were sprayed. Treated plants and controls were maintained in a greenhouse for sixteen days, whereupon all species were compared to controls and visually rated for response to treatment. The ratings are based on a numerical scale extending from 0=no injury, to 10=complete kill. The accompanying descriptive symbols have the following meanings:

B=burn;
C=chlorosis and/or necrosis;
D=defoliation;
E=emergence inhibition;
G=growth retardation;
H=formative effects;
S=albinism;
U=unusual pigmentation;
X=axillary stimulation; and
6Y=abscised buds or flowers.

The ratings for the compounds tested by this procedure are presented in Table A. It will be seen that certain of the compounds tested are highly active herbicides and that several have potential utility for weed control in crops such as wheat and soybeans.

Compounds of Table A

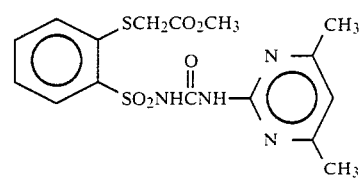

Compound 1

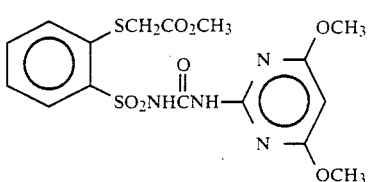

Compound 2

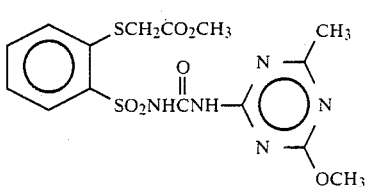

Compound 3

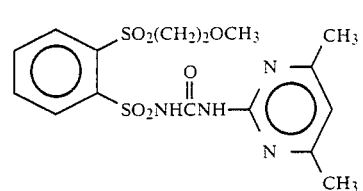

Compound 4

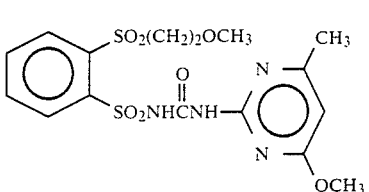

Compound 5

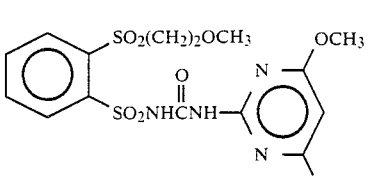

Compound 6

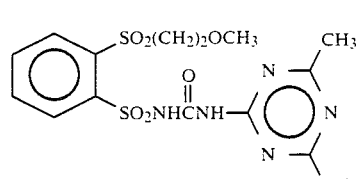

Compound 7

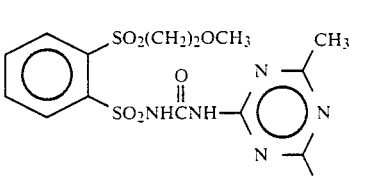

Compound 8

-continued
Compounds of Table A
Compound 9
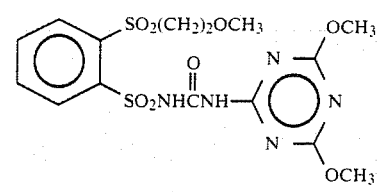
Compound 10
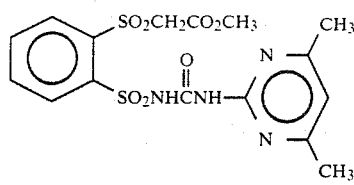
Compound 11
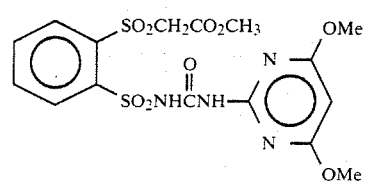
Compound 12
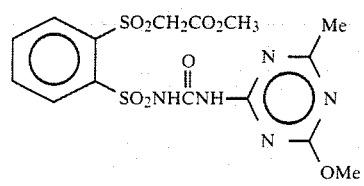
Compound 13
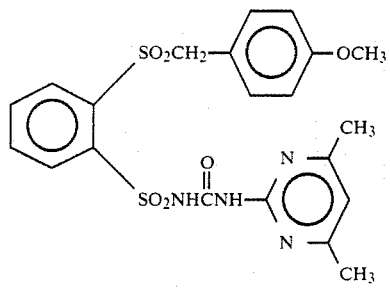
Compound 14
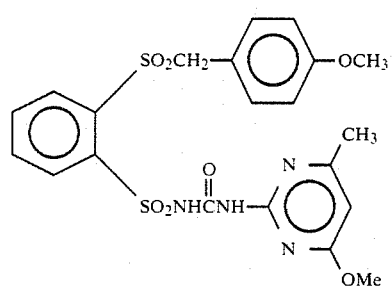
-continued
Compounds of Table A
Compound 15
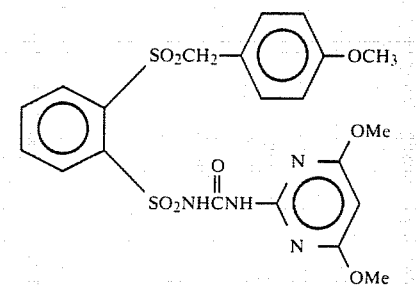
Compound 16
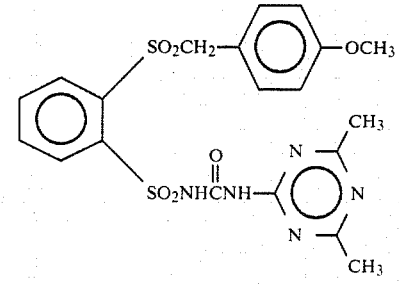
Compound 17
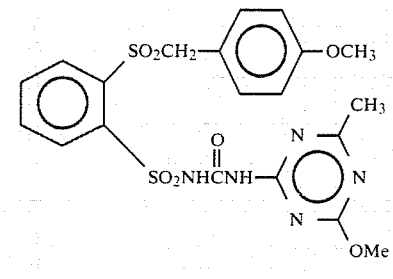
Compound 18
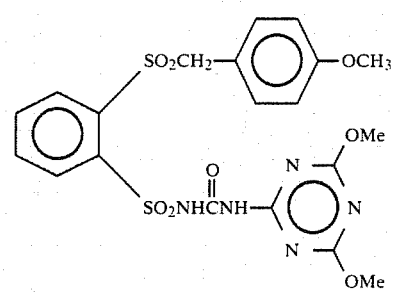
Compound 19
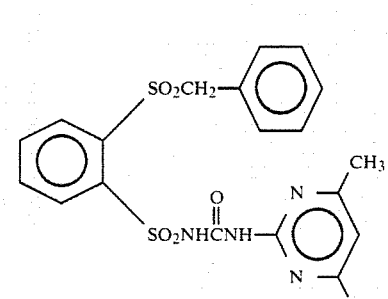

-continued
Compounds of Table A
Compound 20
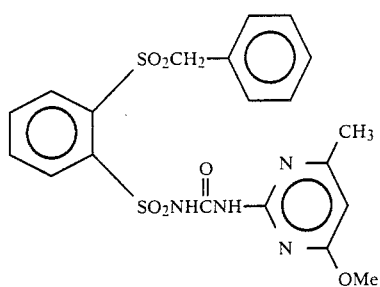
Compound 21
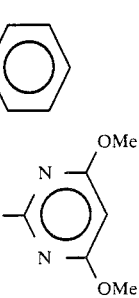
Compound 22
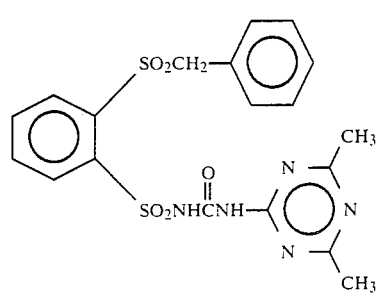
Compound 23
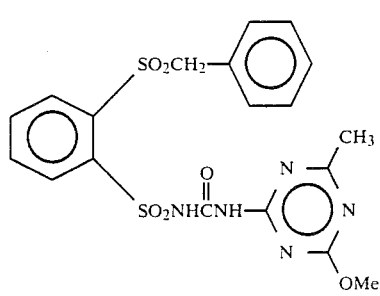
Compound 24
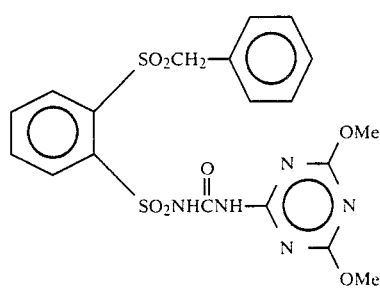
-continued
Compounds of Table A
Compound 25
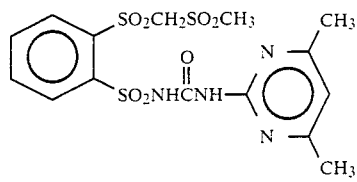
Compound 26
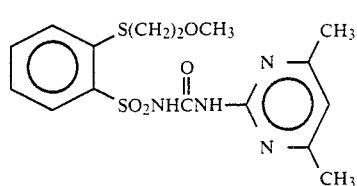
Compound 27
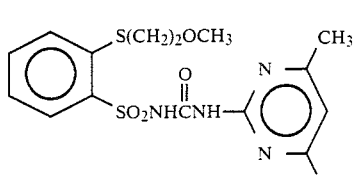
Compound 28
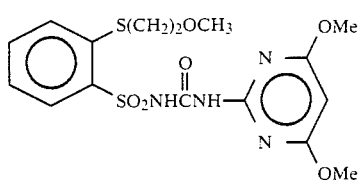
Compound 29
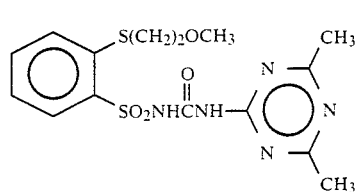
Compound 30
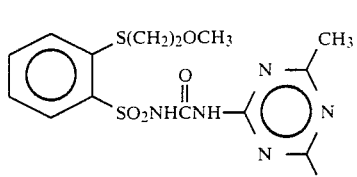
Compound 31
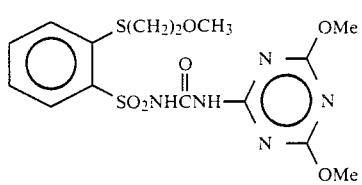
Compound 32
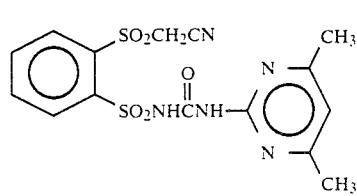

-continued
Compounds of Table A
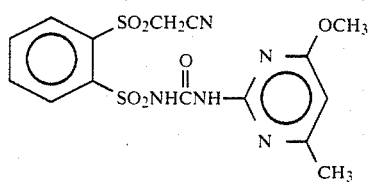 Compound 33
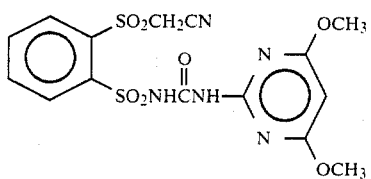 Compound 34
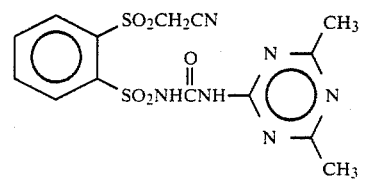 Compound 35
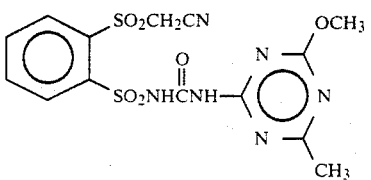 Compound 36
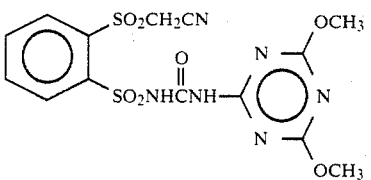 Compound 37
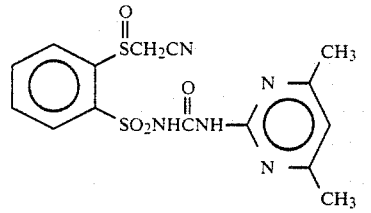 Compound 38
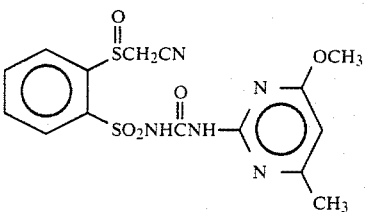 Compound 39
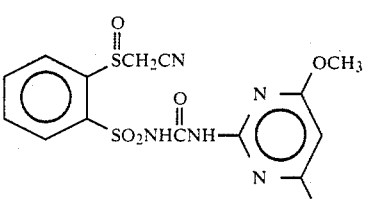 Compound 40
-continued
Compounds of Table A
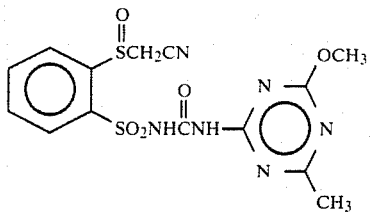 Compound 41
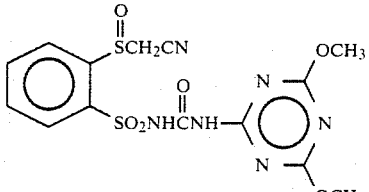 Compound 42
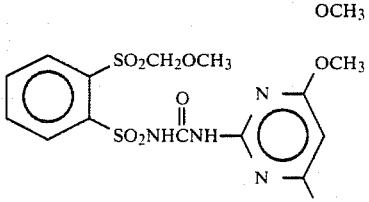 Compound 43
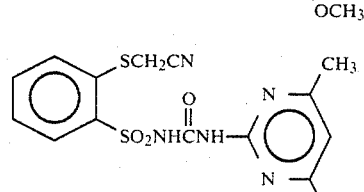 Compound 44
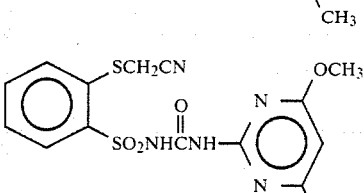 Compound 45
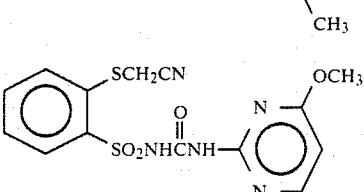 Compound 46
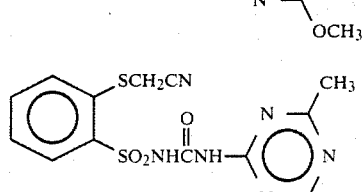 Compound 47
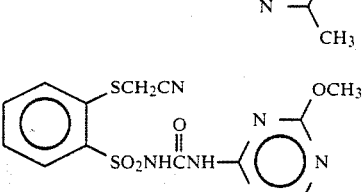 Compound 48
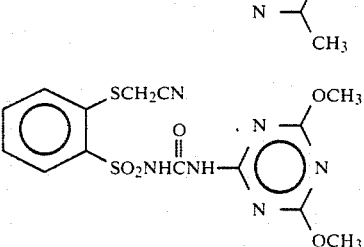 Compound 49

TABLE A

| Rate kg/ha | Cmpd. 1 | | Cmpd. 2 | | Cmpd. 3 | | Cmpd. 4 | Cmpd. 5 | Cmpd. 6 | Cmpd. 7 | Cmpd. 8 | Cmpd. 9 | Cmpd. 10 | Cmpd. 11 | Cmpd. 12 |
|---|---|---|---|---|---|---|---|---|---|---|---|---|---|---|---|
| | 2 | .05 | 2 | .05 | 2 | .05 | 0.4 | 0.4 | 0.4 | 0.4 | 0.4 | 0.4 | 2 | 0.4 | 2 |
| POST-EMERGENCE | | | | | | | | | | | | | | | |
| Bush bean | 4S,8G,6Y | 3C,3H,6Y | 5S,9G,6Y | 5S,7G,6Y | 4S,8G,6Y | 4S,8G,6Y | 3C,8G,6Y | 9C | 7C,9G,6Y | 5C,9G,6Y | 9C | 5C,9G,6Y | 8D,9G,6Y | 1C,3G | 10D,9G,6Y |
| Cotton | 5C,8G | 2C,4G | 5C,9G | 4C,7G | 3C,3H,7G | 6C,9G | 4C,9G | 2U,5C,9G | 2U,5C,9G | 5C,9G | 2U,5C,9G | 2U,4C,9G | 6C,9G | 9C | 2U,4C,9G |
| Morningglory | 1C,5G | 0 | 1C | 2C | 1C | 1C | 5C,9G | 10C | 6C,9G | 4C,9G | 10C | 9C | 9C | 9C | 3C,9G |
| Cocklebur | 1C,4G | 0 | 1C,4H | 1C | 0 | 0 | 5C,9G | 9C | 5C,9G | 3C,3H | 10C | 9C | 4C,9G | 3C,9G | 10C |
| Cassia | 1C,4G | 0 | 1C,4G | 2G | 0 | 0 | 4C,6H | 6C,9G | 3C,6G | 2C,8G | 4C,8H | 4C,8H | 4C,9G | 9C | 9C |
| Nutsedge | 2G | 0 | 1C,5G | 0 | 5H | 0 | 9G | 2C,9G | 5C,9G | 6C,9G | 2C,7G,7X | 2C,9G | 2C,6G | 2C,8G | 9C |
| Crabgrass | 2C,5G | 1C | 1C,6G | 4G | 0 | 0 | 2C,9G | 5C,9G | 6C,9G | 9C | 9C | 2C,8G | 5C,9G | 9C | 9C |
| Barnyardgrass | 5C,9H | 1C,5H | 5C,9H | 5C,8H | 5H | 1C,5G | 6C,9H | 9C | 9C | 6C,9H | 9C | 9C | 6U,9G | 9C | 5C,9G |
| Wild Oats | 8G | 0 | 1C | 0 | 0 | 0 | 4C,9G | 4C,9G | 4C,9G | 2C,9G | 9G | 1C,9G | 6U,9G | 4C,9G | 5U,9C |
| Corn | 1C,7G | 5H | 1C,6H | 2H | 5H | 0 | 1C,8G | 2C,9G | 3C,9G | 1C,8G | 1C,8G | 1C,9G | 5U,9G | 6U,9G | 7U,9G |
| Soybean | 2U,9G | 4G | 5C,9G | 2C,2H | 0 | 1C,4H | 4U,9G | 7U,9G | 7U,9C | 3U,9G | 5U,10C | 6U,9G | 5U,9G | 9C | 9C |
| Rice | 2C,6G | 2G | 8G | 1C,4G | 0 | 1C,5G | 6C,9G | 5C,9G | 6C,9G | 3C,9G,5X | 5C,9G | 5C,9G | 5C,9G | 6C,9G | 9C |
| Sorghum | 1C,8G | 4G | 1C,9G | 2C,7H | 0 | 0 | 7C,9G | 7C,9G | 6C,9G | 6C,9G | 6C,9G | 6C,9G | 9C | 7U,9G | 6U,9G |
| Sorghum | 1C,9G | 2C,7H | 1C,9G | 2C,7H | 0 | 0 | 3C,9G | 5U,9G | 10C | 5U,9G | 5U,9G | 2U,9G | 7U,9G | | |

| Rate kg/ha | Cmpd. 13 | Cmpd. 14 | Cmpd. 15 | Cmpd. 16 | Cmpd. 17 | Cmpd. 18 | Cmpd. 19 | Cmpd. 20 | Cmpd. 21 | Cmpd. 22 |
|---|---|---|---|---|---|---|---|---|---|---|
| | 2 | 2 | 2 | 2 | 2 | 2 | 0.05 | 0.05 | 0.05 | 0.05 |
| POST-EMERGENCE | | | | | | | | | | |
| Bush bean | 1C | 2S,3G,6Y | 2C | 1C | 4C,9G,6Y | 1C | 0 | 1H | 1H | 0 |
| Cotton | 0 | 2C | 2C,3H | 3B | 3C,3H | 1C | 0 | 1H | 0 | 0 |
| Morningglory | 0 | 1C | 1C,3G | 1B,2C | 3C,3H | 1C,2H | 1B | 2H | 0 | 0 |
| Cocklebur | 1H | 2H | 3C,5H | 1H | 1H | 1H | 3H | 0 | 5G | 0 |
| Cassia | 2G | 0 | 4G | 1C,3G | 3C,4H | 1C | 0 | 0 | 0 | 0 |
| Nutsedge | 0 | 0 | 5H | 5G | 0 | 0 | 0 | 0 | 0 | 0 |
| Crabgrass | 0 | 3G | 0 | 0 | 2C | 1H | 0 | 0 | 0 | 0 |
| Barnyardgrass | 2G | 1H | 5C,9H | 0 | 3C,6H | 1H | 0 | 1H | 0 | 0 |
| Wild Oats | 0 | 0 | 1C | 0 | 0 | 0 | 0 | 0 | 0 | 0 |
| Corn | 0 | 3G | 2G | 0 | 2G | 0 | 0 | 0 | 0 | 0 |
| Soybean | 2G | 0 | 4G | 0 | 2U,9G | 1C,4H | 1B | 2C,7H | 0 | 0 |
| Rice | 0 | 2G | 1C,4G | 0 | 2C,6G | 1C,1H | 0 | 0 | 0 | 0 |
| Wheat | 1C | 3H | — | 9G | — | 3G | 3G | 1H | 0 | 0 |
| Sorghum | | | 2C,9H | | 9G | 1C,3G | 0 | 0 | 0 | 0 |

| Rate kg/ha | Cmpd. 23 | Cmpd. 23 | Cmpd. 24 | Cmpd. 25 | Cmpd. 26 | Cmpd. 27 | Cmpd. 28 | Cmpd. 29 | Cmpd. 30 | Cmpd. 31 | Cmpd. 32 | Cmpd. 33 |
|---|---|---|---|---|---|---|---|---|---|---|---|---|
| | 2 | 0.05 | 0.05 | 0.05 | 0.4 | 0.4 | 0.4 | 0.4 | 0.4 | 0.4 | 0.05 | 0.05 |
| POST-EMERGENCE | | | | | | | | | | | | |
| Bush bean | 1C | 1C,2G | 0 | 0 | 9D,9G,6Y | 9C | 9C | 2C,9G | 10C | 1C,3G | 1C | 6Y |
| Cotton | 0 | 1H | 0 | 1H | 4C,9G | 5C,9G | 4C,9G | 2C,9G | 5C,9G | 5C,9G | 2G | 1C,1H |
| Morningglory | 0 | 0 | 1H | 0 | 5C,9G | 9C | 1C | 1C | 9C | 5C,8H | 1C | 1H |
| Cocklebur | 1H | 0 | 0 | 0 | 5C,9H | 9C | 10C | 3C,9H | 4C,8G | 9C | 0 | 2C,5H |
| Cassia | 0 | 2H | 0 | 0 | 4C,7G | 9C | 5C,9G | 2C | 9C | 2C,7G | 2G | 2H |
| Nutsedge | 0 | 0 | 0 | 0 | 2C,9G | 4C,9G | 9C | 3G | 2C | 6G | 0 | 2C,3H |
| Crabgrass | 0 | 0 | 0 | 2C | 3C,8G | 4C,9H | 1C | 1C | 7G | 2G | 2G | 5G |
| Barnyardgrass | 0 | 1C | 0 | 3C,6H | 5C,9H | 10C | 9C | 2C,6H | 2C,9G | 3H | 0 | 4G |
| Wild Oats | 0 | 0 | 0 | 0 | 5C,9H | 6C,6G | 9C | 1C,3G | 5G | 2C,6H | 3H | 4H |
| Corn | 0 | 3G | 0 | 0 | 2C,9G | 2C,9G | 4C,9G | 0 | 3G | 5C,9H | 0 | 1C |
| Soybean | 2G | 0 | 1C,4G | 0 | 5U,9G | 3U,9C | 10C | 5U,9C | 2C,7H | 2C,3G | 0 | 2G |
| Rice | 2G | 0 | — | — | 9C | 5C,9G | 5C,9G | 3C,9G | 7G | 6G | 5U,9H | 3C,8G |
| Corn | 1C | 1H | 2C,9H | 9G | | | | | | | | 3C,5H |
| Soybean | | | | | | | | | | 2C,9H | 1H | 1C |

TABLE A-continued

POST-EMERGENCE

| | Cmpd. 34 | | Cmpd. 35 | | Cmpd. 36 | | Cmpd. 37 | | Cmpd. 38 | | Cmpd. 39 | | Cmpd. 40 | | Cmpd. 41 |
|---|---|---|---|---|---|---|---|---|---|---|---|---|---|---|---|
| Rate kg/ha | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 |
| Bush bean | 0 | | 0 | | 1H | | 1H | | 1C | | 5C,9G,6Y | | 1H | | 4C,9G,6Y |
| Cotton | 1C,4G | 1C,2H | 0 | 1C,1H | 1C,1H | | 0 | | 0 | | 3C,8G | 2H,2C | 2C | | 3C,7G |
| Morningglory | 2C,6H | 1C | 0 | 1C | 2C | | 1H | | 1C | | 4C,8H | 5C,8G | 4C,6H | | 6H,3C |
| Cocklebur | 2G | 0 | 0 | 4G | 0 | | 0 | | 0 | | 6C,9G | 1C | 2C | | 1C,6H |
| Cassia | 3C | 1C | 0 | 3C,5G | 1C | | 0 | | 0 | | 4C,8H | 4C,5H | 2C,5H | | 2C,5H |
| Nutsedge | 5G | 0 | 0 | 5G | 2H | | 3G | | 0 | | 5G | 2C,9G | 3C,8G | | 3G |
| Crabgrass | 8G | 5G | 0 | 6G | 0 | | 2G | | 0 | | 5G | 2C,5G | 0 | | 3G |
| Barnyardgrass | 9H | 3G | 0 | 2C,8H | 2H | | 2H | | 1C | | 3C,9H | 9H | 1C,3G | | 3C,9H |
| Wild Oats | 2C,8G | 4H | 0 | 3G | 6H | | 0 | | 0 | | 2C,9H | 2G | 0 | | 0 |
| Wheat | 4G,5X | 2C,6H | 0 | 2G | 2G | | 0 | | 2G | | 2C,9H | 0 | 0 | | 0 |
| Corn | 2C,6H | 5G | 0 | 8H | 1C,2H | | 3G | | 0 | | 1C,7G | 1C,3G | 1U,9G | | 1U,9G |
| Soybean | 1C,7G | 3G | 0 | 7G | 3G | | 0 | | 0 | | 2C,9H | 1C,2H | 1C,2G | | 5C,9G |
| Rice | 2C,8G | 2C,5G | 0 | 8G | 2G | | 2G | | 0 | | 2C,9G | 5G | 0 | | 6G |
| Sorghum | 2C,9G | 2C,8G | 0 | 2C,9G | 0 | | 2G | | 0 | | 3C,9G | 2C,9G | 4C,9H | | 2C,9G |
| Sugar beets | 4C,9G | 3C,6G | 0 | 4C,7H | 0 | | 0 | | 0 | | 4C,9H | 3C,8H | 3C,8H | | 3C,8H |

| | Cmpd. 41 | Cmpd. 42 | | Cmpd. 43 | | Cmpd. 44 | | Cmpd. 45 | | Cmpd. 46 | | Cmpd. 47 | | Cmpd. 48 | | Cmpd. 49 |
|---|---|---|---|---|---|---|---|---|---|---|---|---|---|---|---|---|
| Rate kg/ha | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 |
| Bush bean | 5S,7G,6Y | 2C,6Y | 0 | 0 | | 5C,9G,6Y | | 9C | | 6C,9G,6Y | | 4C,7G,6Y | | 5C,9G,6Y | | 6C,9G,6Y |
| Cotton | 1C | 0 | 2C | 3C,3H | 2C | 5C,9G | | 6C,9G | | 3C,9G | | 4C,9G | | 4C,8G | | 5C,9G |
| Morningglory | 1C | 0 | 2G | 4C,5H | 2G | 9C | | 9C | | 5C,8G | | 4C,9G | | 4C,8G | | 9C |
| Cocklebur | 0 | 1C | 0 | 4G | 2G | 10C | | 10C | | 6C,9G | | 2C,8G | | 1C | | 9G |
| Cassia | 1C | 3C,3H | 1C | 3C,6H | 2C | 5C,9G | | 5C,8G | | 5C,9G | | 9G,5C | | 3C | | 6C,9G |
| Nutsedge | 2G | 0 | 0 | 2C,6G | 2G | 4C,5G | | 6C,8G | | 5C,9G | | 2G | | 6G | | 8G |
| Crabgrass | 1C | 2G | 0 | 0 | 1C | 2C,8G | | 2C | | 3C | | 4C,8G | | 3C | | 4C,8G |
| Barnyardgrass | 0 | 2C,3H | 2C | 2C,9G | 2C | 5C,9H | | 5C,9G | | 3C,9H | | 5C,9H | | 5C,9H | | 5C,9G |
| Wild Oats | 0 | 0 | 0 | 1C,7G | 0 | 4C,9G | | 4C,9G | | 5C,9H | | 2C,8G | | 3C,9H | | 1C |
| Wheat | 4H | 2C,4H | 1C | 1C,5G | 0 | 9G | | 2C,8G | | 4C,9G | | 3G | | 0 | | 2G |
| Corn | 3C,5G | 2C,8H | 2H | 2U,9G | 1C | 10C | | 8G | | 2U,8H | | 5U,9C | | 2U,8G | | 3C,9G |
| Soybean | 0 | 2C,8H | 0 | 3C,9G | 2H | 10C | | 9C | | 10C | | 9C | | 5C,9G | | 5C,9G |
| Rice | 2C,9H | 2G | 0 | 9C | 0 | 4C,9G | | 4C,9G | | 6C,9G | | 5C,9G | | 7G | | 1C,9G |
| Sorghum | 2C,9H | 2C,8H | 0 | 9G | 2G | 4C,8G | | 4C,8G | | 1C,9G | | 4C,9G | | 2C,9G | | 5C,9G |
| Sugar beets | 4C,7H | 3C,8H | 1C,3H | 4C,7H | 2C | 4C,6H | | 2C,8G | | 4C,9G | | 4C,9G | | 4C,9G | | 5C,9G |

PRE-EMERGENCE

| | Cmpd. 1 | Cmpd. 2 | Cmpd. 3 | Cmpd. 4 | Cmpd. 5 | Cmpd. 6 | Cmpd. 7 | Cmpd. 8 | Cmpd. 9 | Cmpd. 10 | Cmpd. 11 | Cmpd. 12 |
|---|---|---|---|---|---|---|---|---|---|---|---|---|
| Rate kg/ha | .05 | .05 | .05 | .4 | .4 | .4 | .4 | .4 | .4 | 2 | .4 | 2 |
| Morningglory | 1C | 2C,6G | 6G | 9C | 9C | 9C | 9H | 9C | 9C | 9C | 9G | 9G |
| Cocklebur | 5H | 7H | 8H | 9C | 9H | 9H | 9H | 9H | 9H | 9G | 9H | 9H |
| Cassia | 0 | 1C | 5G | 3C,9G | 5C,9G | 3C,9G | 2C | 4C,9G | 3C,8G | 2C,9G | 9G | 9G |
| Nutsedge | 0 | 7G | 0 | 10E | 10E | 10E | 1C,4G | 6G | 2C,5G | 10E | 10E | 4C,9G |
| Crabgrass | 1C | 1C | 0 | 3C,9G | 5C,9G | 3C,9G | 5G | 5C,9G | 5C,9G | 3C,9H | 5G | 5G |
| Barnyardgrass | 1C | 2C,6H | 2C | 4C,9G | 6C,9G | 4C,9G | 5C,8G | 5C,9G | 3C,8G | 2C,9H | 3C,9H | 5C,9H |
| Wild Oats | 0 | 2C | 0 | 4C,8G | 6C,9H | 6C,9H | 2C | 4C,8G | 3C,9H | 3C,9H | 3C,9H | 4C,9G |

TABLE A-continued

| | Cmpd. 13 | Cmpd. 14 | Cmpd. 15 | Cmpd. 16 | Cmpd. 17 | Cmpd. 18 | Cmpd. 19 | Cmpd. 20 | Cmpd. 21 | Cmpd. 22 | Cmpd. 23 |
|---|---|---|---|---|---|---|---|---|---|---|---|
| Wheat | 9G | 0 | 5G | 1C | 4G | 0 | 9H | 2C,9G | 1C,9G | 2C,9H | 3C,9G |
| Corn | 2C,8G | 2C | 3C,8G | 2C,3G | 2C,9G | 2C | 9H | 2C,9G | 3C,9H | 9G | 2C,9G |
| Soybean | 0 | 0 | 2C,1H | 0 | 0 | 0 | 9H | 2C,2H | 3C,8H | 9H | 9H |
| Rice | 9H | 2C | 6C,9H | 2C,6G | 5C,9H | 3G | 10E | 9H | 10E | 10E | 10E |
| Sorghum | 2C,9G | 2C | 5C,9G | 2C,8G | 2C,9H | 1C | 6C,9H | 3C,9H | 6C,9H | 10E | 10E |
| Rate kg/ha | 2 | 2 | 2 | 2 | 2 | 2 | 2 | 2 | 2 | 0.05 | 2 |

PRE-EMERGENCE

| | Cmpd. 23 | Cmpd. 24 | Cmpd. 25 | Cmpd. 26 | Cmpd. 27 | Cmpd. 28 | Cmpd. 29 | Cmpd. 30 | Cmpd. 31 | Cmpd. 32 | Cmpd. 33 |
|---|---|---|---|---|---|---|---|---|---|---|---|
| Morningglory | 4G | 9H | 9G | 9H | 5H | 2C,9H | 2C,5G | 2H | 9G | 0 | 0 |
| Cocklebur | 8H | 9H | 9H | 9H | 7H | 9H | 3C,9H | 7H | — | 0 | 0 |
| Cassia | 1C | 5G | 5C,8G | 2C | 2C | 5C,9H | 2C,8G | 0 | 2C,8G | 0 | 0 |
| Nutsedge | 0 | 5G | 10E | 0 | 0 | 5C,9H | 1C,7G | 0 | 10E | 0 | 0 |
| Crabgrass | 0 | 2G | 1C | 0 | 2G | 10E | 2C,5G | 0 | 2C,5G | 0 | 0 |
| Barnyardgrass | 4C | 3C,9H | 5C,9G | 4C | 2G | 9H | 5C,9H | 0 | 4C,9G | 5G | 3G |
| Wild Oats | 2H | 2C,8G | 8G | 4G | 1C,4G | 10E | 2C,9H | 5C,9H | 8G | 4G,1C | 5G |
| Wheat | 4G | 2C,8G | 2C,8G | 3G | 8G | 10E | 5C,9H | 2C,8G | 3C | 3G | 5G |
| Corn | 3C,8G | 2U,9G | 3C,8G | 8G | 3C,8G | 10E | 4G | 0 | 3C,9H | 2G | 1C,6G |
| Soybean | 2C,6G | 7H | 2C,7G | 2C,7G | 1H | 8H | 4C,9H | 5C,9H | 1C | 4G | 5G |
| Rice | 1C,2G | 2C,9G | 2C,5G | 2C,5G | 2C,7G | 9H | 2C,2H,5G | 9H | 5C,9H | 2G | 1C,5G |
| Sorghum | 2C,7G | 1U,9G | 2C,3G | 2C,5G | 2C,8H | 10E | 10E | 7C,9H | 4C,9H | 2C | 3G |
| Sugar beets | 2C,5G | 5C,9H | 0 | 3C,8G | 2C,8H | 5C,9H | 1C,9H | — | 3C,9H | 0 | 2C,8G |
| Rate kg/ha | 0.05 | 0.4 | 0.4 | 0.4 | 0.4 | 0.4 | 0.4 | 0.4 | 0.4 | 0.4 | 0.05 |

PRE-EMERGENCE

| | Cmpd. 34 | Cmpd. 35 | Cmpd. 36 | Cmpd. 37 | Cmpd. 38 | Cmpd. 39 | Cmpd. 40 | Cmpd. 41 |
|---|---|---|---|---|---|---|---|---|
| Morningglory | 8G | 3C,6H | 0 | 2H | 1C | 9G | 2C,6H | 9G |
| Cocklebur | 8H | 3C,6H | 2G | 8G | 6G | 9H | — | 9G |
| Cassia | 7G | 1C | 5G | — | 2C | 8G | 2C | 2C,8G |
| Nutsedge | 8G | 0 | 0 | 0 | 8G | 5G | 0 | 0 |
| Crabgrass | 1C | 3C,6G | 2G | 1C | 1C | 2G | 2C,5G | 3G |
| Barnyardgrass | 2C,5G | 4C,5H | 1C | 2C | 5G | 1C,5G | 4C,9H | 5G |
| Wild Oats | 3C,6G | 2C,6G | 1C | 1C | 1C | 3C,9H | 9G | 1C,6G |
| Wheat | 6G | 1C | 0 | 2G | 5G | 3G | 2C,9G | 5G |
| Corn | 6G | 4C,7H | 0 | 1C | 2G | 4G | 2C,5H | 1C,5G |
| Soybean | 1C,3G | 2C,2H | 2C,3G | 3C,5G | 5C,9H | 1C | 10E | 3G |
| Rice | 3G | 5C,8G | 0 | 3C,6G | 9H | 1C,3G | 2C,9H | 2C,8G |
| Sorghum | | 3C,5H | | 2C,6G | 1C | 2C,5G | 10E | 5G |
| Soybean | | | | 1C | 0 | 6G | 0 | |
| Rate kg/ha | 0.4 | 0.05 | 0.4 | 0.05 | 0.4 | 0.05 | 0.05 | 0.4 |

TABLE A-continued

| | Cmpd. 41 | | Cmpd. 42 | | Cmpd. 43 | | Cmpd. 44 | | Cmpd. 45 | | Cmpd. 46 | | Cmpd. 47 | | Cmpd. 48 | | Cmpd. 49 | |
|---|---|---|---|---|---|---|---|---|---|---|---|---|---|---|---|---|---|---|
| Rate kg/ha | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 |
| Rice | | 4C,9H | | 2C,5G | | 2G | | 1C,4G | | 0 | | 10E | | 5C,9H | | 3C | | 3C,7H |
| Sorghum | | 4C,9H | | 2C,5G | | 2C,5G | | 1C,5G | | 0 | | 7C,9H | | 4C,9H | | 3C,9H | | 2C,9G |
| Sugar beets | | 9G | | 7G | | 10E | | 8G | | 0 | | 10E | | 10E | | 10E | | 10E |

| | Cmpd. 41 | Cmpd. 42 | Cmpd. 43 | Cmpd. 44 | Cmpd. 45 | Cmpd. 46 | Cmpd. 47 | Cmpd. 48 | Cmpd. 49 |
|---|---|---|---|---|---|---|---|---|---|
| Rate kg/ha | 0.05 | 0.4 | 0.4 | 0.4 | 0.4 | 0.05 | 0.4 | 0.05 | 0.4 |

PRE-EMERGENCE

| | Cmpd. 41 | Cmpd. 42 | Cmpd. 43 | Cmpd. 44 | Cmpd. 45 | Cmpd. 46 | Cmpd. 47 | Cmpd. 48 | Cmpd. 49 |
|---|---|---|---|---|---|---|---|---|---|
| Morningglory | 4G | 7G | 2G | 2C,9G | 9G | 8G | 3C,9G | 8G | 9G |
| Cocklebur | — | 8H | 2G | — | 9H | 9H | 9H | 9H | 9H |
| Cassia | 2H | 7G | 4G,2C | 9G | 9G | 9G | 7G | 9G | 9G |
| Nutsedge | 0 | 0 | 0 | 10E | 10E | 10E | 10E | 8G | 7G |
| Crabgrass | 0 | 0 | 0 | 2C,9G | 4C,9G | 3C,8G | 1C | 7G | 7G |
| Barnyardgrass | 0 | 6H | 0 | 4C,9H | 5C,9H | 5C,9H | 4C,9H | 5G | 9H,5C |
| Wild Oats | 0 | 0 | 0 | 5C,9H | 5C,9H | 6C,9H | 3C,8G | 3G | 3C,6H |
| Wheat | 0 | 5G | 0 | 2C,9H | 5C,9H | 1C,9G | 2C,8G | 3G | 8G |
| Corn | 1C,4G | 1C,8G | 1C,3G | 3C,9H | 10H | 2U,9G | 2C,9G | 2C,8G | 9G |
| Soybean | 1H | 1C,1H | 0 | 10E | 9H | 7H | 4C,7H | 3C,7H | 9H |
| Rice | 0 | 10E | 2C,7H | 10E | 10E | 9H | 10E | 3C,8H | 9H |
| Sorghum | 2C,8G | 2C,7H | 5G | 9H | 6C,9H | 2C,9H | 5C,9G | 5C,9H | 5C,9H |
| Sugar beets | 0 | 9G | 6G | 10E | 10E | 10E | 10E | 10E | 10E |

TEST B

Two plastic bulb pans were filled with fertilized and limed Fallsington silt loam soil. One pan was planted with corn, sorghum, Kentucky bluegrass and several grassy weeds. The other pan was planted with cotton, soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pensylvanicum*), pigweed (*Amaranthus retroflexus*), morningglory (*Ipomoea hederacea*), cassia (*Cassia tora*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugar beets. The above four containers were treated pre-emergence with several test compounds within the scope of the invention.

Twenty-eight days after treatment, the plants were evaluated and visually rated for response to the chemical treatments utilizing the rating system described previously for Test A. The data are summarized in Table B. Note that certain compounds have high pre-emergence activity.

TABLE B

PRE-EMERGENCE ON FALLSINGTON SILT LOAM

| | Compound 1 | | Compound 2 | | Compound 4 | | Compound 5 | | Compound 6 | | Compound 7 | | Compound 8 | |
|---|---|---|---|---|---|---|---|---|---|---|---|---|---|---|
| Rate kg/ha | .060 | .250 | .060 | .250 | .030 | .120 | .030 | .120 | .030 | .120 | .030 | .120 | .030 | .120 |
| Crabgrass | 0 | 0 | 0 | 0 | 0 | 2G | 7G,3H | 8G,5H | 7G,5H | 9G,5H | 0 | 0 | 0 | 4G |
| Barnyardgrass | 3G | 2G | 3G | 3G | 2G | 8G,8C | 9G,9C | 10C | 9C,8C | 10C | 2G | 2G | 6G | 7G |
| Sorghum | 0 | 0 | 2G | 2G | 5G,3H | 9G,5H | 10C | 10C | 10C | 10E | 0 | 3G,2H | 8G,5H | 10C |
| Wild Oats | 0 | 0 | 0 | 0 | 3G | 6G,3H | 7G,5H | 8G,5H | 6G | 8G,3H | 0 | 0 | 5G | 7G,5H |
| Johnsongrass | 0 | 0 | 0 | 0 | 4G | 6G,3H | 9G,5H | 9G,5H | 8G,5H | 10C | 2G | 2G | 5G,2H | 9G,5H |
| Dallisgrass | 0 | 0 | 0 | 0 | 0 | 5G | 7G | 8G,3H | 7G | 9G,5H | 0 | 0 | 0 | 0 |
| Giant foxtail | 0 | 0 | 0 | 0 | 5G,3H | 7G,5H | 10C | 10C | 8G,5H | 10C | 0 | 0 | 0 | 4G,3H |
| Ky. bluegrass | 0 | 0 | 0 | 0 | 3G | 6G,5C | 8G,9C | 10C | 8G,7C | 10C | 0 | 0 | 0 | 7G,5C |
| Cheatgrass | 0 | 0 | 0 | 0 | 3G | 5G | 10C | 10E | 8G | 10E | — | 0 | 0 | 5G |
| Sugar beets | 3G | 2G | 2G | 4G | 0 | 4G | 9G,9C | 10C | 7G,5C | 10C | 0 | 0 | 3G | 7G,5H |
| Corn | 0 | 0 | 0 | 0 | 0 | 4G | 7G,5H | 8G,5H | 7G,5H | 9G,5H | 0 | 0 | 5G,5H | 8G,5H |
| Mustard | 7G | 5G | 4G | 6G,3C | 0 | 8G,3H | 10C | 10C | 9G,5C | 10C | 0 | 0 | 2G | 7G,5C |
| Cocklebur | 0 | 0 | 0 | 0 | 0 | 2G | 4G,3H | 7G,3H | 5G,3H | 8G,5H | 0 | 0 | 1C | 5G |
| Pigweed | 0 | 3G | 6C | 4C | 0 | 3G | 5G | 8G,5C | 8G,5C | 9G,9C | 0 | 0 | 0 | 5G |
| Nutsedge | 0 | 0 | 0 | 2G | 0 | 8G | 5G | 10E | 8G | 10E | 0 | 0 | 0 | 5G |
| Cotton | 0 | 0 | 0 | 2G | 0 | 3G | 4G | 5G,5H | 4G,2H | 8G | 0 | 0 | 4G | 7G,5H |
| Morningglory | 3G | 2G | 0 | 2G | 0 | 5G,5H | 8G | 8G,3C | 6G,2H | 8G,2C | 0 | 0 | 5G,3H | 8G,5C |
| Cassia | 0 | 3G | 0 | 4G | 0 | 0 | 3G,2C | 6G,5H | 5G,2C | 9G,5C | 0 | 0 | 0 | 4G,3C |
| Teaweed | 0 | 0 | 0 | 0 | 0 | 0 | 1C | 4G,2C | 3G | 5G,3H | 0 | 0 | 0 | 0 |
| Velvetleaf | 6G,3H | 3G | 0 | 2G | 0 | 0 | 5G,3H | 7G,5H | 3H | 9G,9C | 0 | 0 | 0 | 5G,3H |
| Jimsonweed | 0 | 0 | 0 | 0 | 0 | 0 | 7G,8C | 9G,9C | 7G | 7G | 0 | 0 | 0 | 5G,2C |
| Soybean | 0 | 0 | 0 | 3G | 0 | 4G,5H | 5G,5H | 9G,5H | 5G,5H | 9G,5H | 0 | 0 | 0 | 5G,5H |
| Rice | 3G | 3G | 4G | 6G | 5G,3H | 7G,5H | 8G,5H | 10E | 10E | 10E | 0 | 3G | 8G,5H | 10C |
| Wheat | 0 | 0 | 0 | 0 | 0 | 3G | 6G | 7G | 6G | 8G,3C | 0 | 0 | 3G | 3G |

| | Compound 9 | | Compound 10 | | Compound 11 | | Compound 12 | | Compound 14 | | Compound 15 | | Compound 17 | |
|---|---|---|---|---|---|---|---|---|---|---|---|---|---|---|
| Rate kg/ha | .030 | .120 | .030 | .120 | .030 | .120 | .030 | .120 | 0.06 | 0.25 | 0.06 | 0.25 | 0.06 | 0.25 |
| Crabgrass | 0 | 2G | 0 | 0 | 5G | 8G,8C | 0 | 2G | 0 | 0 | 0 | 0 | 0 | 0 |
| Barnyardgrass | 0 | 8G,4C | 0 | 5G | 7G | 9G,6C | 5G | 7G | 0 | 0 | 0 | 0 | 0 | 0 |
| Sorghum | 6G,5H | 8G,5H | 0 | 6G,3H | 8G,3H | 10E | 6G,3H | 9G,8C | 0 | 0 | 0 | 0 | 0 | 0 |
| Wild Oats | 4G | 6G | 0 | 6G | 5G | 7G,3H | 0 | 4G | 0 | 0 | 0 | 0 | 0 | 0 |
| Johnsongrass | 4G | 7G,5H | 0 | 3G | 8G,3U | 8G,3H | 3G | 6G,5H | 0 | 0 | 0 | 0 | 0 | 0 |
| Dallisgrass | 0 | 0 | 0 | 0 | 4G | 6G | 0 | 0 | 0 | 0 | 0 | 0 | 0 | 0 |
| Giant foxtail | 0 | 0 | 0 | 0 | 6G,3H | 8G,3H | 0 | 3G | 0 | 0 | 0 | 0 | 0 | 0 |
| Ky. bluegrass | 3G | 8G,3C | 0 | 3G | 8G,3H | 10C | 0 | 6G | 0 | 0 | 0 | 0 | 0 | 0 |
| Cheatgrass | 0 | 0 | 0 | 3G | 7G | 10E | 0 | 5G | 0 | 0 | 0 | 0 | 0 | 0 |
| Sugar beets | 5G | 7G,8C | 0 | 4G | 7G,3H | 8G,8C | 0 | 5G | 0 | 0 | 0 | 2G | 0 | 0 |
| Corn | 3G | 4G | 0 | 0 | 6G | 8G,5H | 5G,3H | 7G,3H | 0 | 0 | 0 | 3G | 0 | 0 |
| Mustard | 0 | 3G | 4G | 7G | 8G,3C | 9G,9C | 0 | 0 | 0 | 6G,5H | 0 | 6G,5H | 0 | 3G |
| Cocklebur | 0 | 5G,3H | 0 | 0 | 4G | 7G | 0 | 0 | 0 | 0 | 0 | 0 | 0 | 0 |
| Pigweed | 0 | 5G,3C | 0 | 0 | 7G | 6G | 0 | 0 | 0 | 0 | 0 | 0 | 0 | 0 |
| Nutsedge | 0 | 3G | 0 | 0 | 3G | 8G | 0 | 0 | 0 | 0 | 0 | 0 | 0 | 0 |
| Cotton | 0 | 4G,3H | 0 | 3G | 3G | 6G | 0 | 2G | 0 | 0 | 0 | 0 | 0 | 0 |
| Morningglory | 0 | 7G,5H | 0 | 3G | 0 | 8G,3C | 0 | 4G,3C | 0 | 0 | 0 | 0 | 0 | 0 |
| Cassia | 0 | 3G,1C | 0 | 0 | 3G | 8G | 0 | 0 | 0 | 0 | 0 | 0 | 0 | 0 |
| Teaweed | 0 | 0 | 0 | 0 | 0 | 8G | 0 | 0 | 0 | 0 | 0 | 0 | 0 | 0 |
| Velvetleaf | 0 | 3G,2H | 0 | 0 | 4G | 7G,5H | 0 | 0 | 0 | 0 | 0 | 0 | 0 | 0 |
| Jimsonweed | 0 | 0 | 0 | 0 | 5G | 7G | 0 | 0 | 0 | 0 | 0 | 0 | 0 | 0 |
| Soybean | 0 | 2G | 0 | 0 | 2G | 5G,3H | 0 | 0 | 0 | 0 | 0 | 0 | 0 | 0 |
| Rice | 8G,5H | 10E | 0 | 6G,3H | 10E | 10E | 4G | 4G | 0 | 0 | 0 | 0 | 0 | 0 |
| Wheat | 0 | 0 | 0 | 5G | 4G | 6G | 0 | 0 | 0 | 0 | 0 | 0 | 0 | 0 |

TEST C

The test chemical, dissolved in a non-phytotoxic solvent, was applied as an overall spray to the foliage and surrounding soil of selected plant species. One day after treatment, plants were observed for rapid burn injury. Approximately fourteen days after treatment, all species were visually compared to untreated controls and rated for response to treatment. The rating system was as described previously for Test A. The data are presented in Table C.

All plant species were seeded in Woodstown sandy loam soil and grown in a greenhouse. The following species were grown in soil contained in plastic pots (25 cm diameter by 13 cm deep): soybeans, cotton, alfalfa, corn, rice, wheat, sorghum, velvetleaf (*Abutilon theophrasti*), sesbania (*Sesbania exaltata*), Cassia (*Cassia tora*), morningglory (*Ipomoea hederacea*), jimsonweed (*Datura stramonium*), cocklebur (*Xanthium pensylvanicum*), crabgrass (*Digitaria sp.*), nutsedge (*Cyperus rotundus*), barnyardgrass (*Echinochloa crusgalli*), giant foxtail (*Setaria faberii*) and wild oats (*Avena fatua*). The following species were grown in soil in a paper cup (12 cm diameter by 13 cm deep): sunflower, sugar beets, and mustard. All plants were sprayed approximately 14 days after planting.

The results of this study indicate that the test compound has utility for post-emergence weed control in wheat.

TABLE C

| Over-the-Top Soil/Foliage Treatment | | | |
|---|---|---|---|
| | Compoud 8 | | |
| Rate kg/ha | 0.063 | 0.016 | 0.004 |
| Soybeans | 9G,7C | 9G,6C | 8G |
| Velvetleaf | 10C | 9G,5C | 8G,3C |
| Sesbania | 9G,3C | 6G,5C | 9G |
| Cassia | 7G,4C | 5G,4C | 8G |
| Cotton | 10C | 9G,2C | 8G |
| Morningglory | 9G,7C | 9G,5C | 9G |
| Alfalfa | 9G,7C | 8G,6C | 6G |
| Jimsonweed | 8G,5C | 8G,5C | 6G |
| Cocklebur | 9G,2C | 9G,2C | 9G,1C |
| Sunflower | 9G,8C | 5G,7C | 2C |
| Mustard | 9G,8C | 6G,5C | 1C |
| Sugar beets | 9G,3C | 8G,3C | 2G |
| Corn | 9G,5U | 6G,2U | 6G |
| Crabgrass | 0 | 0 | 0 |
| Rice | 9G,8C | 8G,7C | 8G,7C |
| Nutsedge | 0 | 0 | 0 |
| Barnyardgrass | 10C | 2G,1H | 0 |
| Wheat | 0 | 0 | 0 |
| Giant foxtail | 6G | 0 | 0 |
| Wild Oats | 3G | 0 | 0 |
| Sorghum | 7G,1C | 6G,1C | 5G |

What is claimed is:
1. A compound of the formula

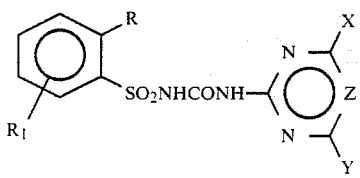

wherein
R is $S(O)_n CH(R_2)A$;
A is $OCH_2CH_2OCH_3$, $CH_2OCH_2CH_2OCH_3$, $CO_2R_3$, $CH_2CO_2R_3$; CN, $CH_2CH_2CN$,

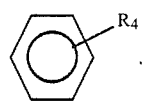

$CH_2OH$, $CH(OH)CH_3$, $CH_2CH_2OH$, $C(O)CH_3$, $CH_2C(O)CH_3$, CHO, $CH(OCH_3)_2$ or

$R_1$ and $R_4$ are independently H, F, Cl, Br, $CH_3$, $OCH_3$, $CF_3$ or $NO_2$;
$R_2$ is H or $CH_3$;
$R_3$ is $C_1$-$C_2$ alkyl;
n is 0, 1 or 2;
p is 0, 1 or 2;
X is $CH_3$, $OCH_3$ or Cl;
Y is $CH_3$, $C_2H_5$, $CH_2OCH_3$, $OCH_3$, $OC_2H_5$, $NH_2$, $NHCH_3$ or $N(CH_3)_2$; and
Z is CH;
and their agriculturally suitable salts.

2. Compounds of claim 1 where
A is $CO_2R_3$ or CN;
$R_1$ is H; and
X is not Cl.

3. Compounds of claim 1 where Y is $NH_2$, $NHCH_3$ or $N(CH_3)_2$.

4. The compound of claim 1 which is N-[(4,6-dimethylpyrimidin-2-yl)aminocarbonyl]-2-(cyanomethylthio)benzenesulfonamide.

5. The compound of claim 1 which is N-[(4-methoxy-6-methylpyrimidin-2-yl)aminocarbonyl]-2-(cyanomethylthio)benzenesulfonamide.

6. The compound of claim 1 which is N-[(4,6-dimethoxypyrimidin-2-yl)aminocarbonyl]-2-(cyanomethylthio)benzenesulfonamide.

7. The compound of claim 1 which is N-[(4,6-dimethylpyrimidin-2-yl)aminocarbonyl]-2-(2-(methoxy-2-oxoethylsulfonyl)benzenesulfonamide.

8. The compound of claim 1 which is N-[(4,6-dimethoxypyrimidin-2-yl)aminocarbonyl]-2-(2-methoxy-2-oxoethylsulfonyl)benzenesulfonamide.

9. A composition suitable for controlling the growth of undesired vegetation which comprises an effective amount of a compound of claim 1 and at least one of the following: surfactant, solid or liquid diluent.

10. A composition suitable for controlling the growth of undesired vegetation which comprises an effective amount of a compound of claim 2 and at least one of the following: surfactant, solid or liquid diluent.

11. A composition suitable for controlling the growth of undesired vegetation which comprises an effective amount of a compound of claim 3 and at least one of the following: surfactant, solid or liquid diluent.

12. A method for controlling the growth of undesired vegetation which comprises applying to the locus to be protected an effective amount of a compound of claim 1.

13. A method for controlling the growth of undesired vegetation which comprises applying to the locus to be protected an effective amount of a compound of claim 2.

14. A method for controlling the growth of undesired vegetation which comprises applying to the locus to be protected an effective amount of a compound of claim 3.

* * * * *